US012778873B2

(12) United States Patent
Gu et al.

(10) Patent No.: US 12,778,873 B2
(45) Date of Patent: Nov. 3, 2026

(54) PEPTIDES AND THEIR USE IN THE TREATMENT OF INFLAMMATION

(71) Applicant: ENLITISA (SHANGHAI) PHARMACEUTICAL CO., LTD., Shanghai (CN)

(72) Inventors: Ming Gu, Jiangyin City (CN); Maoqian Song, Jiangyin City (CN); Jan-Christer Janson, Uppsala (SE); Bengt Ingemar Samuelsson, Solna (SE)

(73) Assignee: ENLITISA (SHANGHAI) PHARMACEUTICAL CO., LTD., Shanghai (CN)

( * ) Notice: Subject to any disclaimer, the term of this patent is extended or adjusted under 35 U.S.C. 154(b) by 862 days.

(21) Appl. No.: 17/781,571

(22) PCT Filed: Dec. 2, 2020

(86) PCT No.: PCT/CN2020/133436

§ 371 (c)(1),
(2) Date: Jun. 9, 2022

(87) PCT Pub. No.: WO2021/110061

PCT Pub. Date: Jun. 10, 2021

(65) Prior Publication Data

US 2024/0218016 A1 Jul. 4, 2024

(30) Foreign Application Priority Data

Dec. 2, 2019 (WO) ................ PCT/CN2019/122391

(51) Int. Cl.

| | |
|---|---|
| ***A61K 8/64*** | (2006.01) |
| ***A61K 8/73*** | (2006.01) |
| ***A61K 9/00*** | (2006.01) |
| ***A61K 9/06*** | (2006.01) |
| ***A61K 38/00*** | (2006.01) |
| ***A61P 1/04*** | (2006.01) |
| ***A61P 11/00*** | (2006.01) |
| ***A61P 17/00*** | (2006.01) |
| ***A61P 29/00*** | (2006.01) |
| ***A61Q 19/00*** | (2006.01) |
| ***C07K 7/06*** | (2006.01) |
| ***C07K 7/08*** | (2006.01) |
| ***C07K 9/00*** | (2006.01) |

(52) U.S. Cl.

CPC ................ *A61K 8/64* (2013.01); *A61K 8/735* (2013.01); *A61K 9/0014* (2013.01); *A61K 9/06* (2013.01); *A61P 1/04* (2018.01); *A61P 11/00* (2018.01); *A61P 17/00* (2018.01); *A61P 29/00* (2018.01); *A61Q 19/00* (2013.01); *C07K 7/06* (2013.01); *C07K 7/08* (2013.01); *C07K 9/00* (2013.01); *A61K 38/00* (2013.01)

(58) Field of Classification Search

CPC ............ A61K 8/64; A61K 38/00; C07K 9/00; A61P 17/00

See application file for complete search history.

(56) References Cited

U.S. PATENT DOCUMENTS

| | | | | |
|---|---|---|---|---|
| 4,585,585 | A | 4/1986 | Waite | |
| 4,908,404 | A | 3/1990 | Benedict et al. | |
| 5,015,677 | A | 5/1991 | Benedict et al. | |
| 5,024,933 | A | 6/1991 | Yang et al. | |
| 5,229,490 | A | 7/1993 | Tam et al. | |
| 5,616,311 | A * | 4/1997 | Yen | A61K 9/5169 977/797 |
| 2017/0190746 | A1* | 7/2017 | Cha | A61L 24/0015 |
| 2018/0221444 | A1* | 8/2018 | Janson | A61K 8/64 |
| 2018/0228873 | A1* | 8/2018 | Samuelsson | A61P 17/04 |
| 2021/0309696 | A1* | 10/2021 | Samuelsson | A61K 31/47 |
| 2023/0113836 | A1 | 4/2023 | Gu et al. | |
| 2024/0124521 | A1 | 4/2024 | Janson et al. | |
| 2024/0218016 | A1 | 7/2024 | Gu et al. | |

FOREIGN PATENT DOCUMENTS

| | | | |
|---|---|---|---|
| BR | 112018013246 | A2 | 12/2018 |
| CN | 108348636 | A | 7/2018 |
| CN | 110139662 | A | 8/2019 |
| CN | 110312513 | A | 10/2019 |
| CN | 112236440 | A | 1/2021 |

(Continued)

OTHER PUBLICATIONS

Waite, 1987, Nature's underwater adhesive specialist, Int J Adhesion and Adhesives, 7(1): 9-14.*

Burzio et al., 2000, Cross-Linking in Adhesive Quinoproteins: Studies with Model Decapeptides, Biochemistry, 39: 11147-11153.*

Fang et al., 2007, Functional Group Approaches to Prodrugs: Functional Groups in Peptides, Chapter 3.7, pp. 965-988, Prodrugs: Challenges and Rewards Part 1, Eds Stella, Borchardt, Hageman, Oliyai, Maag, and Tilley.*

International Search Report and Written Opinion for corresponding Application No. PCT/CN2020/133436 (mailed Feb. 25, 2021).

Sever and Wilker, "Synthesis of Peptides Containing DOPA (3, 4-dihydroxyphenylalanine)," Tetrahedron 57:6139-6146 (2001).

(Continued)

*Primary Examiner* — Amber D Steele

(74) *Attorney, Agent, or Firm* — Troutman Pepper Locke LLP (Rochester)

(57) ABSTRACT

A compound comprising the amino acid sequence:

$Xaa_1$-$Xaa_2$-Lys-$Xaa_3$-Ser-$Xaa_5$-$Xaa_6$-$Xaa_7$-$Xaa_8$-$Xaa_9$-$Xaa_{10}$-$Xaa_{11}$-$Xaa_{12}$ wherein $Xaa_1$ through $Xaa_{12}$ have meanings given in the description, as well as regioisomers, stereoisomers, and pharmaceutically- or cosmetically-acceptable salts of said peptide compounds. The compounds are particularly useful in the treatment of conditions characterised by inflammation, including wounds, burns, and disorders of the mucosa, such as anorectal diseases, inflammatory bowel diseases, gynaecological diseases and dental diseases.

20 Claims, 1 Drawing Sheet

Specification includes a Sequence Listing.

(56) References Cited

FOREIGN PATENT DOCUMENTS

| | | | | |
|---|---|---|---|---|
| EP | 0359996 A2 | 3/1990 | | |
| EP | 0359996 B1 | 4/1994 | | |
| EP | 2990412 A1 | 3/2016 | | |
| JP | 2004508338 A | 3/2004 | | |
| JP | 2004513897 A | 5/2004 | | |
| JP | 2018513879 A | 5/2018 | | |
| KR | 101677097 B1 | 11/2016 | | |
| WO | 88/07076 A1 | 9/1988 | | |
| WO | 96/39128 A1 | 12/1996 | | |
| WO | WO 96/39128 | * 12/1996 | | A61K 9/64 |
| WO | 2000/015789 A1 | 3/2000 | | |
| WO | 2002/020033 A1 | 3/2002 | | |
| WO | 2002/036160 A2 | 5/2002 | | |
| WO | 03/008376 A2 | 1/2003 | | |
| WO | 2005/118831 A2 | 12/2005 | | |
| WO | 2007/124593 A1 | 11/2007 | | |
| WO | 2009/001220 A2 | 12/2008 | | |
| WO | 2010/038220 A1 | 4/2010 | | |
| WO | 2012/067837 A1 | 5/2012 | | |
| WO | 2016/168743 A1 | 10/2016 | | |
| WO | 2017/011982 A1 | 1/2017 | | |
| WO | 2017011984 A1 | 1/2017 | | |
| WO | 2017/028777 A1 | 2/2017 | | |
| WO | 2017/076495 A1 | 5/2017 | | |
| WO | 2017/088177 A1 | 6/2017 | | |
| WO | 2017115853 A1 | 7/2017 | | |
| WO | 2019/007355 A1 | 1/2019 | | |
| WO | 2019/007356 A1 | 1/2019 | | |
| WO | 2019/011286 A1 | 1/2019 | | |
| WO | 2019/059504 A1 | 3/2019 | | |
| WO | 2018/100174 A1 | 6/2019 | | |
| WO | 2019/173777 A1 | 9/2019 | | |
| WO | 2019/228307 A1 | 12/2019 | | |
| WO | 2020/052677 A1 | 3/2020 | | |
| WO | 2021/047648 A1 | 3/2021 | | |
| WO | 2021110061 A1 | 6/2021 | | |

OTHER PUBLICATIONS

Fichman et al., "The Use of the Calcitonin Minimal Recognition Module for the Design of DOPA-Containing Fibrillar Assemblies," Nanomaterials 4:726-740 (2014).
Liu et al., "Biomimetic Adhesives and Coatings Based on Mussel Adhesive Proteins," Springer International Publishing Switzerland, A.M. Smith (ed.), Biological Adhesives, 345-378 (2016).
Dewan et al., "Antimicrobial Action of Prototypic Amphipathic Cationic Decapeptides and Their Branched Dimers," Biochemistry 48:5642-5657 (2009).
Zhu et al., "Composition, Working Mechanism and Application of Mussel Adhesive Protein," Advances in Marine Science 32(4):560-568 (2014).
Gao et al., "Review on Mussel Adhesiive Protein," Journal of Anhui Agr. Sci. 39(32):19860-19862 (2011).
Yamamoto H., "Synthesis and Adhesive Studies of Marine Polypeptides," Chem. Soc., Perkin Trans. 1:613-618 (1987).
Dalsin et al., "Mussel Adhesive Protein Mimetic Polymers for the Preparation of Nonfouling Surfaces," J. Am. Chem. Soc. 125:4253-42 (2003).
Xiao et al., "Rebounding Triad (Severe Itching, Dryness and Burning) After Facial Corticosteroid Discontinution Defines a Specific Class of Corticosteroid-dependent Dermatitis," J. Dermatol. 42(2):697-702 (2015).
Lu et al., "Facial Corticosteroid Addictive Dermatitis in GuiyangCity, China," Clin. Exp. Dermatol. 35(6):618-621 (2010).
Waite J. H., "Marine Adhesive Proteins: Natural Composite Thermosets," Int. J. Bio. Macromol. 12(2):139-144 (1990).
Kanyalkar et al., "Conformation of a Model Peptide of the Tandem Repeat Decapeptide in Mussel Adhesive Protein by NMR and MD Simulations," Biomaterials 23:389-396 (2002).
Waite J. H., "Evidence for a Repeating 3,4-Dihydroxyphenylalanine- and Hydroxyproline-containing Decapeptide in the Adhesive Protein of the Mussel, *Mytilus edulis* L.," J. Bio. Chem. 258:2911-2915 (1983).
International Search Report and Written Opinion for corresponding Application No. PCT/CN2020/114828 (mailed Dec. 14, 2020).
International Search Report and Written Opinion for corresponding Application No. PCT/CN2019/105830 (mailed Jun. 15, 2020).
Tam J.P., "Synthetic Peptide Vaccine Design: Synthesis and Properties of a High-density Multiple Antigenic Peptide System," Proc. Natl. Acad. Sci. USA 85(15):5409-5413 (1988).
Rao et al., "Synthesis of Peptide Dendrimer," J. Am. Chem. Soc. 116(15):6975-6976 (1994).
Brokx et al., "Designing Peptide-based Scaffolds as Drug Delivery Vehicles," J. Control. Release 78(1-3):115-123 (2002).
International Search Report and Written Opinion for International Application No. PCT/CN2020/133439 (mailed Mar. 4, 2021).
Khunmanee et al., "Crosslinking Method of Hyaluronic-Based Hydrogel for Biomedical Applications," J. Tissue Eng. 8:1-16 (2017).
Foureman et al., "Chemical Mutagenesis Testing in *Drosophila*," Environ. Mol. Mutagen. 23(1):51-63 (1994).
Loo et al., "Bioprinting Synthetic Self-assembling Peptide Hydrogels for Biomedical Applications," Biomed. Mater. 11(1):014103 (2016).
Lee et al., "Target-specific Delivery of siRNA by Stabilized Calcium Phosphate Nanoparticles Using DOPA-Hyaluronic Acid Conjugate," J. Control. Release 192:122-130 (2014).
International Search Report and Written Opinion for International Application No. PCT/CN2020/133438 (mailed Mar. 8, 2021).
Borchardt et al., "Optimizing Oral Absorption of Peptides Using Prodrug Strategies," Journal of Controlled Release 62:231-238 (1999).
Taylor et al., "Polarographic and Spectrophotometric Investigation of Iron (III) Complexation to 3,4-Dihydroxyphenylalanine-Containing Peptides and Proteins from *Mytilus edulis*," Inorganic Chemistry 33(25):5819-5824 (1994).
Burzio et al., "Cross-Linking in Adhesive Quinoproteins: Studies with Model Decapeptides," Biochem. 39(36):11147-11153 (2000).
Quan et al., "Mussel-Inspired Catechol-Functionalized Hydrogels and Their Medical Applications," Molecules 24:1-27 (2019).
Waite J. H., "Nature's Underwater Adhesive Specialist," Int. J. Adhesion and Adhesives 7(1):9-14 (1987).
Silverman et al., "Understanding Marine Mussel Adhesion," Marine Biotechnology, Springer Verlag, NE 9(6):661-681 (2007).
Hwang et al., "Promotion of osteoblast proliferation on complex coacervation-based hyaluronic acid—recombinant mussel adhesive protein coatings on titanium," Biomaterials, Elsevier, Amsterdam, NL 31(6):1080-1084 (2010).
Nakashima et al., "Enzymatic Control Over Coacervation," Methods in Enzymology 646:353-389 (2021).
Costello et al., "A Review of the Current Status and Concept of the Emerging Implications of Zinc and Zinc Transporters in the Development of Pancreatic Cancer," Pancreat Disord Ther., Suppl 4:S4-002 (2013).
Hersh et al., "Unmet Medical Need in Infectious Diseases," Clinical Infectious Diseases 54(11):1677-78 (2012).
Mullin, "Ebola Outbreak Rages on as Drug Development Remains Slow," Fierce Biotech (2014).

* cited by examiner

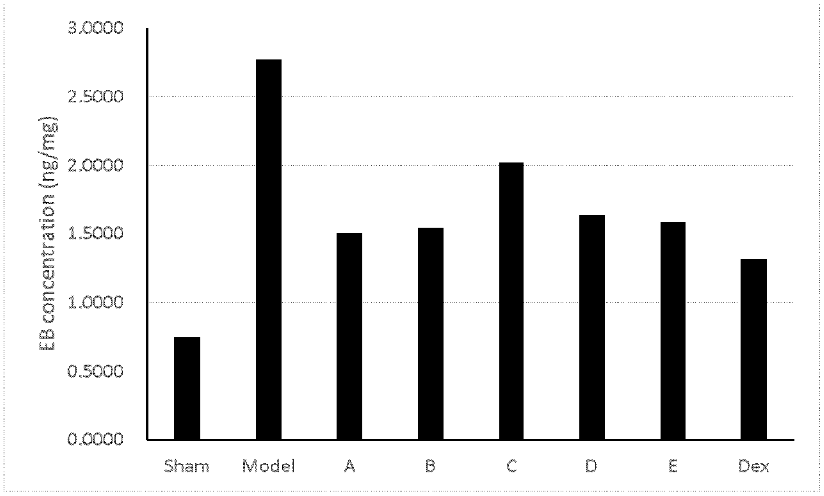
3.0000
2.5000
2.0000
1.5000
1.0000
0.5000
0.0000
EB concentration (ng/mg)
Sham
Model
A
B
C
D
E
Dex

PEPTIDES AND THEIR USE IN THE TREATMENT OF INFLAMMATION

This application is a national stage application under 35 U.S.C. § 371 of International Application No. PCT/CN2020/133436, filed Dec. 2, 2020, which claims priority benefit of International Application No. PCT/CN2019/122391, filed Dec. 2, 2019.

FIELD OF THE INVENTION

This invention relates to new peptides, the use of such peptides in human medicine, and to pharmaceutical compositions comprising them. In particular, the invention relates to the use of those peptides and compositions in the treatment of e.g. inflammation.

SEQUENCE LISTING

The instant application contains a Sequence Listing which has been submitted electronically in ASCII format and is hereby incorporated by reference in its entirety. Said ASCII copy, created on May 5, 2026, is named REPLACEMENT_SEQUENCE_LISTING_147432.001470.txt and is 38,086 bytes in size.

BACKGROUND AND PRIOR ART

Inflammation is typically characterized as a localised tissue response to e.g. invasion of microorganisms, certain antigens, damaged cells or physical and/or chemical factors. The inflammatory response is normally a protective mechanism which serves to destroy, dilute or sequester both the injurious agent and the injured tissue, as well as to initiate tissue healing.

Inflammation may result from physical trauma, infection, some chronic diseases (e.g. psoriasis and autoimmune diseases, such as rheumatoid arthritis) and/or chemical and/or physiological reactions to external stimuli (e.g. as part of an allergic response). A complex series of events may be involved, in which inflammatory mediators increase blood flow and dilation of local blood vessels, resulting in redness and heat, the exudation of fluids, often resulting in localised swelling, leukocytic migration into the inflamed area, and pain.

Many conditions/disorders are characterized by, and/or are caused by, abnormal, tissue-damaging inflammation. Such conditions are typically characterized by activation of immune defence mechanisms, resulting in an effect that is more harmful than beneficial to the host, and are generally associated with varying degrees of tissue redness or hyperemia, swelling, hyperthermia, pain, itching, cell death, tissue destruction, cell proliferation and/or loss of function. Examples include inflammatory bowel diseases, rheumatoid arthritis, multiple sclerosis, psoriasis, glomerulonephritis and transplant rejection.

Typically, a complex series of events results in inflammatory changes such as increased blood flow through dilation of local blood vessels, resulting in redness and heat, the extravasation of leukocytes and plasma, often resulting in localised swelling, activation of sensory nerves (resulting in pain in some tissues) and loss of function. These inflammatory changes are triggered by a cascade of cellular and biochemical events involving cells like neutrophils, monocytes, macrophages and lymphocytes together with inflammatory mediators such as vasoactive amines, cytokines, complement factors and reactive oxygen species.

Amongst other things, inflammation plays a key role in the wound healing process. Wounds and burns can therefore be classified as conditions with which inflammation is associated. Traditional thinking in the art is that anti-inflammatory drugs should not be applied directly to open wounds, as this would be detrimental to the progress of wound healing.

Fibrosis is defined by the excessive accumulation of fibrous connective tissue (components of the extracellular matrix (ECM) such as collagen and fibronectin) in and around inflamed or damaged tissue. Although collagen deposition is typically a reversible part of wound healing, it can often evolve into a progressively irreversible fibrotic response if tissue injury is severe, or if the wound-healing response itself becomes dysregulated. Furthermore, fibrogenesis is known to be a major cause of morbidity and mortality in many chronic inflammatory diseases, as well as end-stage liver disease, kidney disease, idiopathic pulmonary fibrosis (IPF) and heart failure. It is also a pathological feature of many chronic autoimmune diseases, such as scleroderma, rheumatoid arthritis, Crohn's disease, ulcerative colitis, myelofibrosis and systemic lupus erythematosus. Fibrosis may also influence the pathogenesis of many progressive myopathies, metastasis and graft rejection.

Mussel adhesive protein (MAP), also known as *Mytilus edulis* foot protein (mefp), is a protein that is secreted by marine shellfish species, such as *Mytilus edulis, Mytilus coruscus* and *Perna viridis*. Eleven identified separate adhesive protein subtypes have been derived from mussels, including the collagens pre-COL-P, pre-COL-D and pre-COL-NG; the mussel feet matrix proteins PTMP (proximal thread matrix protein) and DTMP (distal thread matrix protein); and mfp proteins mfp-2 (sometimes referred to as "mefp-2", hereinafter used interchangeably), mfp-3/mefp-3, mfp-4/mefp-4, mfp-5/mefp-5, mfp-6/mefp-6 and, most preferably mfp-1/mefp-1 (see, for example, Zhu et al., *Advances in Marine Science,* 32, 560 (2014) and Gao et al., *Journal of Anhui Agr. Sci.,* 39, 19860 (2011)).

A significant portion of mefp-1 consists of 70 to 90 tandem repeats of the decapeptide: Ala-Lys-Pro-Ser-Tyr-Xaa-Xaa-Thr-Xaa-Lys (SEQ ID No: 1; see Waite, *Int. J. Adhesion and Adhesives,* 7, 9 (1987)). This decapeptide sequence may be isolated as a low molecular weight derivative of naturally-occurring MAPs, or may be synthesized, for example as described by Yamamoto in J. Chem. Soc., Perkin Trans. 1, 613 (1987). See also Dalsin et al., *J. Am. Chem. Soc.,* 125, 4253 (2003). Xaa at positions 6 and 7 represents hydroxyproline (Hyp) residues; and Xaa at position 9 represents 3,4-dihydroxyphenylalanine (DOPA).

Analogues of the decapeptide, notably Ala-Lys-Pro-Ser-Tyr-Xaa-Xaa-Thr-Tyr-Lys (SEQ ID No: 2) have also been disclosed, where Xaa at positions 6 and 7 represents hydroxyproline (Hyp). See, for example, U.S. Pat. No. 5,616,311 and WO 96/39128.

There is a clear need for new and/or improved medicines that may be used in the treatment of inflammation and conditions characterised thereby.

BRIEF DESCRIPTION OF THE DRAWINGS

FIG. 1 shows Evans blue content in rectal and anal tissue indicating vascular permeability of test compounds

DISCLOSURE OF THE INVENTION

According to a first aspect of the invention, there is provided an (isolated) peptide compound of the amino acid sequence:

```
                                        (SEQ ID NO: 3)
W-Lys-X1-Ser-U-X2-Y-G
```

wherein:

- $Xaa_1$ is selected from the group consisting of Lys, Ala and DOPA, optionally comprising an N-terminal 3,4-dihydrocinnamic acid (HCA) residue;
- $Xaa_2$ is optional and selected from the group consisting of Lys, Ala and DOPA;
- $Xaa_3$ is Pro, 3Hyp, 4Hyp, 3,4diHyp, 3,5diHyp, or 4,5diHyp;
- $Xaa_5$ is Tyr or DOPA;
- $Xaa_6$ is Ser, Pro, 3Hyp, 4Hyp, 3,4diHyp, 3,5diHyp, or 4,5diHyp;
- $Xaa_7$ is selected from the group consisting of Lys, Ala, Pro, 3Hyp, 4Hyp, 3,4diHyp, 3,5diHyp, 4,5diHyp, Thr, DOPA and Tyr;
- each of $Xaa_8$, $Xaa_9$, $Xaa_{10}$, and $Xaa_{11}$ is optional and, when present, is selected from the group consisting of Lys, Ala, Pro, 3Hyp, 4Hyp, 3,4diHyp, 3,5diHyp, 4,5diHyp, Thr, DOPA and Tyr; and
- $Xaa_{12}$ may be absent (in which case $Xaa_7$ is the C-terminal amino acid) or $Xaa_{12}$ is DOPA or dopamine (or, more properly, 'a dopamine fragment'),
- as well as regioisomers, stereoisomers, and pharmaceutically- or cosmetically-acceptable salts of said peptide compounds,
- which compounds, regioisomers, stereoisomers and salts are referred to together hereinafter as 'the compounds of the invention'. Hyp as recited with respect to SEQ ID NOS: 3-89 recited herein independently represents 3-hydroxyproline, 4-hydroxyproline, or 5-hydroxyproline. DiHyp as recited with respect to SEQ ID NOS: 3-89 represents 3,4-dihydroxyproline (3,4diHyp), 3,5-dihydroxyproline (3,5diHyp), and 4,5-dihydroxyproline (4,5diHyp). DOPA as recited herein with respect to SEQ ID NOS: 3-89 recited herein represents 3,4-dihydroxyphenylalanine.

As used herein, the terms 'dopamine' and 'dopamine fragment' refer to a structural fragment of formula I,

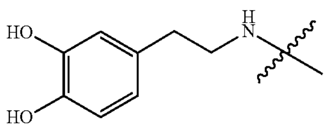

I wherein the squiggly line represents the point of attachment to any of $Xaa_7$, $Xaa_8$, $Xaa_9$, $Xaa_{10}$, and $Xaa_{11}$.

Compounds of the invention that may be mentioned include those in which:

- $Xaa_1$ represents a 1 or 2 amino acid sequence, in which the amino acids are selected from one or more of the group Lys, Ala and DOPA;
- $Xaa_3$ represents Pro;
- $Xaa_6$ represents Ser, Pro, 3Hyp, or 4Hyp; and
- $Xaa_7$ represents Lys, Ala, Pro, 3Hyp, 4Hyp, 3,4diHyp, 3,5diHyp, 4,5diHyp, Thr, DOPA or Tyr; and
- each of $Xaa_8$, $Xaa_9$, $Xaa_{10}$, and $Xaa_{11}$ is optional and, when present, is selected from the group consisting of Lys, Ala, Pro, 3Hyp, 4Hyp, 3,4diHyp, 3,5diHyp, 4,5diHyp, Thr, DOPA and Tyr.

Particular compounds of the invention that may be mentioned are those where G is absent, i.e. of the amino acid sequence:

```
                                        (SEQ ID No: 4)
W-Lys-X1-Ser-U-X2-Y,
```

- wherein $Xaa_1$ represents HCA, HCA-Ala-, HCA-Lys, HCA-Lys-Ala, more preferably DOPA-Lys- or DOPA-Lys-Ala- or, especially, DOPA or DOPA-Ala-; and
- $Xaa_3$, $Xaa_5$, $Xaa_6$, and $Xaa_7$-$Xaa_{11}$ are as hereinbefore defined,
- as well as regioisomers, stereoisomers, and pharmaceutically- or cosmetically-acceptable salts thereof.

Preferred compounds of the invention include those in which:

- $Xaa_3$ represents 3Hyp, 4Hyp, or, more preferably, Pro;
- $Xaa_6$ represents Pro or, more preferably, 3Hyp or 4Hyp;
- $Xaa_1$ represents HCA, HCA-Ala-, preferably Ala, or Lys-Ala- or, more preferably, DOPA or DOPA-Ala-; and/or
- $Xaa_7$ represents Lys, Ala, Pro, 3Hyp, 4Hyp, 3,4diHyp, 3,5diHyp, 4,5diHyp, Thr, DOPA or Tyr;
- each of $Xaa_8$, $Xaa_9$, $Xaa_{10}$, and $Xaa_{11}$ is optional and, when present, is selected from the group consisting of Lys, Ala, Pro, 3Hyp, 4Hyp, 3,4diHyp, 3,5diHyp, 4,5diHyp, Thr, DOPA and Tyr.

More preferably, compounds of the invention also include those in which $Xaa_7$, $Xaa_8$, $Xaa_9$, $Xaa_{10}$, and/or $Xaa_{11}$ represents a 4 amino acid sequence selected from the group -Pro-$Xaa_8$-$Xaa_9$-Lys- (SEQ ID NO: 75) or, more preferably, -Hyp-$Xaa_8$-$Xaa_9$-Lys- (SEQ ID NO: 76) where Hyp is 3Hyp or 4Hyp, and -Thr-$Xaa_8$-$Xaa_9$-Lys- (SEQ ID NO: 77), wherein $Xaa_8$ and $Xaa_9$ are each independently selected from the group Pro or, more preferably, Ala, 3Hyp, 4Hyp, Thr, DOPA and Tyr.

When $Xaa_7$, $Xaa_8$, $Xaa_9$, $Xaa_{10}$, and/or $Xaa_{11}$ represents a 4 amino acid sequence, preferred compounds of the invention include those in which the amino acid sequence defined by $Xaa_7$, $Xaa_8$, $Xaa_9$, $Xaa_{10}$, and/or $Xaa_{11}$ is selected from the group:

```
                                        (SEQ ID NO: 78)
-Pro-Thr-DOPA-Lys-;
                                        (SEQ ID NO: 79)
-Pro-Thr-Tyr-Lys-;
                                        (SEQ ID NO: 80)
-Thr-Tyr-Pro-Lys-; and
                                        (SEQ ID NO: 81)
-Thr-DOPA-Pro-Lys-; and, more preferably,
                                        (SEQ ID NO: 82)
-Hyp-Thr-Tyr-Lys- where Hyp is 3Hyp or 4Hyp;
                                        (SEQ ID NO: 83)
-Hyp-Thr-DOPA-Lys- where Hyp is 3Hyp or 4Hyp;
                                        (SEQ ID NO: 84)
-Hyp-Thr-Ala-Lys- where Hyp is 3Hyp or 4Hyp;
                                        (SEQ ID NO: 85)
-Thr-Tyr-Hyp-Lys- where Hyp is 3Hyp or 4Hyp;
```

-continued

```
                                    (SEQ ID NO: 86)
-Thr-DOPA-Hyp-Lys- where Hyp is 3Hyp or 4Hyp; and

                                    (SEQ ID NO: 87)
-Thr-Ala-Hyp-Lys- where Hyp is 3Hyp or 4Hyp.
```

When $Xaa_7$, $Xaa_8$, $Xaa_9$, $Xaa_{10}$, and/or $Xaa_{11}$ represent a 2 amino acid sequence, preferred compounds of the invention include those in which the amino acid sequence defined by $Xaa_7$, $Xaa_8$, $Xaa_9$, $Xaa_{10}$, and/or $Xaa_{11}$ is selected from the group -Hyp-Thr-, -Thr-Tyr- and -Thr-DOPA-, where Hyp is 3Hyp or 4Hyp.

Other compounds of the invention that may be mentioned include those in which the amino acid sequence defined by $Xaa_7$, $Xaa_8$, $Xaa_9$, $Xaa_{10}$, and/or $Xaa_{11}$ is selected from -Thr-Tyr-Lys-, -Tyr-Pro-Lys-, -DOPA-Pro-Lys-, -Hyp-Thr-Tyr-, -Hyp-Thr-Tyr-Hyp-Lys- (SEQ ID NO: 88) where Hyp is 3Hyp or 4Hyp, and, more preferably, the groups -Thr-Tyr-Hyp-Lys-DOPA- (SEQ ID NO: 89), where Hyp is 3Hyp or 4Hyp and -Hyp-Thr-DOPA, where Hyp is 3Hyp or 4Hyp.

Compounds of the invention that may be mentioned include those in which:

$Xaa_5$ represents Tyr; and $Xaa_1$ and $Xaa_2$ represents DOPA or DOPA-Ala-.

In this respect, further compounds of the invention that may be mentioned include those of the amino acid sequence:

Xaa-Lys-Pro-Ser-Tyr-Xaa-Thr-Ala-Xaa-Lys (SEQ ID No: 5), where Xaa at position 1 is DOPA as defined herein and where Xaa at positions 6 and 9 are Hyp as defined herein;

Xaa-Lys-Pro-Ser-Tyr-Xaa-Xaa-Thr-Ala-Lys (SEQ ID No: 6), where Xaa at position 1 is DOPA as defined herein and where Xaa at positions 6 and 7 are Hyp as defined herein;

Xaa-Ala-Lys-Pro-Ser-Tyr-Xaa-Thr-Tyr-Xaa-Lys (SEQ ID No: 7), where Xaa at position 1 is DOPA as defined herein and where Xaa at positions 7 and 10 are Hyp as defined herein;

Xaa-Ala-Lys-Pro-Ser-Tyr-Xaa-Xaa-Thr-Tyr-Lys (SEQ ID No: 8), where Xaa at position 1 is DOPA as defined herein and where Xaa at positions 7 and 8 are Hyp as defined herein;

Xaa-Ala-Lys-Pro-Ser-Tyr-Xaa-Thr-Xaa-Xaa-Lys (SEQ ID No: 9), where Xaa at positions 1 and 9 is DOPA as defined herein and where Xaa at positions 7 and 10 are Hyp as defined herein;

Xaa-Ala-Lys-Pro-Ser-Tyr-Xaa-Xaa-Thr-Xaa-Lys (SEQ ID No: 10), where Xaa at positions 1 and 10 is DOPA as defined herein and where Xaa at positions 7 and 8 are Hyp as defined herein;

Xaa-Ala-Lys-Pro-Ser-Xaa-Xaa-Thr-Tyr-Xaa-Lys (SEQ ID No: 11), where Xaa at positions 1 and 6 is DOPA as defined herein and where Xaa at positions 7 and 10 are Hyp as defined herein;

HCA-Lys-Pro-Ser-Tyr-Xaa-Xaa-Thr-Ala-Lys (SEQ ID No: 12), where Xaa at positions 6 and 7 are Hyp as defined herein.

Compounds of the invention that may be mentioned include those in which $Xaa_5$ represents Tyr; and $Xaa_1$ and $Xaa_2$ represent HCA or HCA-Ala-.

In this respect, further compounds of the invention that may be mentioned include those of the amino acid sequence:

HCA-Ala-Lys-Pro-Ser-Tyr-Xaa-Thr-Tyr-Xaa-Lys (SEQ ID No: 13), where Xaa at positions 7 and 10 are Hyp as defined herein;

HCA-Ala-Lys-Pro-Ser-Tyr-Xaa-Thr-Xaa-Xaa-Lys (SEQ ID No: 14), where Xaa at position 9 is DOPA as defined herein and where Xaa at positions 7 and 10 are Hyp as defined herein;

HCA-Ala-Lys-Pro-Ser-Xaa-Xaa-Thr-Xaa-Xaa-Lys (SEQ ID No: 15), where Xaa at positions 6 and 9 is DOPA as defined herein and where Xaa at positions 7 and 10 are Hyp as defined herein;

HCA-Ala-Lys-Pro-Ser-Tyr-Xaa-Xaa-Thr-Tyr-Lys (SEQ ID No: 16), where Xaa at positions 7 and 8 are Hyp as defined herein;

HCA-Ala-Lys-Pro-Ser-Tyr-Xaa-Xaa-Thr-Xaa-Lys (SEQ ID No: 17), where Xaa at position 10 is DOPA as defined herein and where Xaa at positions 7 and 8 are Hyp as defined herein;

HCA-Ala-Lys-Pro-Ser-Xaa-Xaa-Xaa-Thr-Xaa-Lys (SEQ ID No: 18), where Xaa at positions 6 and 10 is DOPA as defined herein and where Xaa at positions 7 and 8 are Hyp as defined herein;

HCA-Ala-Lys-Pro-Ser-Xaa-Xaa-Thr-Tyr-Xaa-Lys (SEQ ID No: 19), where Xaa at position 6 is DOPA as defined herein and where Xaa at positions 7 and 10 are Hyp as defined herein;

HCA-Ala-Lys-Pro-Ser-Xaa-Xaa-Xaa-Thr-Tyr-Lys (SEQ ID No: 20), where Xaa at position 6 is DOPA as defined herein and where Xaa at positions 7 and 8 are Hyp as defined herein;

HCA-Lys-Pro-Ser-Tyr-Xaa-Thr-Ala-Xaa-Lys (SEQ ID No: 21), where Xaa at positions 6 and 9 are Hyp as defined herein;

HCA-Lys-Pro-Ser-Xaa-Xaa-Thr-Ala-Xaa-Lys (SEQ ID No: 22), where Xaa at position 5 is DOPA as defined herein and where Xaa at positions 7 and 9 are Hyp as defined herein; and HCA-Lys-Pro-Ser-Xaa-Xaa-Xaa-Thr-Ala-Lys (SEQ ID No: 23), where Xaa at position 5 is DOPA as defined herein and where Xaa at positions 6 and 7 are Hyp as defined herein.

Compounds of the invention that may be mentioned include those in which $Xaa_5$ represents Tyr; and $Xaa_1$ and $Xaa_2$ represent Lys-Ala-.

In this respect, further compounds of the invention that may be mentioned include those of the amino acid sequence:

Lys-Ala-Lys-Xaa-Ser-Tyr-Xaa-Xaa-Thr-Tyr (SEQ ID No: 24), where Xaa at positions 4, 7, and 8 are Hyp as defined herein;

Lys-Ala-Lys-Pro-Ser-Xaa-Xaa-Xaa-Thr-Tyr (SEQ ID No: 25), where Xaa at position 6 is DOPA as defined herein and where Xaa at positions 7 and 8 are Hyp as defined herein;

Lys-Ala-Lys-Pro-Ser-Tyr-Xaa-Xaa-Thr-Tyr (SEQ ID No: 26), Xaa at positions 7 and 8 are Hyp as defined herein;

Lys-Ala-Lys-Xaa-Ser-Xaa-Xaa-Xaa-Thr-Tyr (SEQ ID No: 27), where Xaa at position 6 is DOPA as defined herein and where Xaa at positions 4, 7, and 8 are Hyp as defined herein.

Particular compounds of the invention that may be mentioned from the lists above include those of the amino acid sequence:

Lys-Ala-Lys-Pro-Ser-Tyr-Xaa-Xaa-Thr-Tyr (SEQ ID No: 26), where Xaa at positions 7 and 8 are Hyp as defined herein, and, more preferably, Xaa-Lys-Pro-Ser-Tyr-Xaa-Thr-Ala-Xaa-Lys (SEQ ID No: 5), where Xaa at position 1 is DOPA as defined herein and where Xaa at positions 6 and 9 are Hyp as defined herein;

Xaa-Lys-Pro-Ser-Tyr-Xaa-Xaa-Thr-Ala-Lys (SEQ ID No: 6), where Xaa at position 1 is DOPA as defined herein and where Xaa at positions 6 and 7 are Hyp as defined herein;

Xaa-Ala-Lys-Pro-Ser-Tyr-Xaa-Thr-Tyr-Xaa-Lys (SEQ ID No: 7), where Xaa at position 1 is DOPA as defined herein and where Xaa at positions 7 and 10 are Hyp as defined herein; and Xaa-Ala-Lys-Pro-Ser-Tyr-Xaa-Xaa-Thr-Tyr-Lys (SEQ ID No: 8), where Xaa at position 1 is DOPA as defined herein and where Xaa at positions 7 and 8 are Hyp as defined herein.

Compounds of the invention that may be mentioned include those in which:

$Xaa_5$ represents DOPA; and $Xaa_1$ and $Xaa_2$ represent DOPA or DOPA-Ala-.

In this respect, further compounds of the invention that may be mentioned include those of the amino acid sequence:

Xaa-Lys-Pro-Ser-Xaa-Xaa-Thr-Ala-Xaa-Lys (SEQ ID No: 28), where Xaa at positions 1 and 5 is DOPA as defined herein and where Xaa at positions 6 and 9 are Hyp as defined herein;

Xaa-Lys-Pro-Ser-Xaa-Xaa-Xaa-Thr-Ala-Lys (SEQ ID No: 29), where Xaa at positions 1 and 5 is DOPA as defined herein and where Xaa at positions 6 and 7 are Hyp as defined herein;

Xaa-Ala-Lys-Pro-Ser-Xaa-Xaa-Thr-Xaa-Xaa-Lys (SEQ ID No: 30), where Xaa at positions 1, 6, and 9 is DOPA as defined herein and where Xaa at positions 7 and 10 are Hyp as defined herein;

Xaa-Ala-Lys-Pro-Ser-Xaa-Xaa-Xaa-Thr-Tyr-Lys (SEQ ID No: 31), where Xaa at positions 1 and 6 is DOPA as defined herein and where Xaa at positions 7 and 8 are Hyp as defined herein; and Xaa-Ala-Lys-Pro-Ser-Xaa-Xaa-Xaa-Thr-Xaa-Lys (SEQ ID No: 32), where Xaa at positions 1, 6, and 10 is DOPA as defined herein and where Xaa at positions 7 and 8 are Hyp as defined herein.

Compounds of the invention that may be mentioned include those in which $Xaa_1$ represents Ala.

In this respect, further compounds of the invention that may be mentioned include those of the amino acid sequence:

Ala-Lys-Pro-Ser-Tyr-Xaa-Thr-Tyr-Xaa-Lys (SEQ ID No: 33), where Xaa at positions 6 and 9 is Hyp as defined herein;

Ala-Lys-Pro-Ser-Tyr-Xaa-Thr-Xaa-Xaa-Lys (SEQ ID No: 34), where Xaa at position 8 is DOPA as defined herein and where Xaa at positions 6 and 9 are Hyp as defined herein;

Ala-Lys-Pro-Ser-Xaa-Xaa-Thr-Tyr-Xaa-Lys (SEQ ID No: 35), where Xaa at position 5 is DOPA as defined herein and where Xaa at positions 6 and 9 are Hyp as defined herein; and Ala-Lys-Pro-Ser-Xaa-Xaa-Thr-Xaa-Xaa-Lys (SEQ ID No: 36), where Xaa at positions 5 and 8 is DOPA as defined herein and where Xaa at positions 6 and 9 are Hyp as defined herein.

In a further aspect of the invention, there is provided an (isolated) peptide compound of the amino acid sequence:

(SEQ ID No: 37)
W-Lys-Pro-Ser-U-$X^2$-Y-G, wherein:

$Xaa_{12}$ represents DOPA or, more preferably, 'a dopamine fragment'; and $Xaa_1$, $Xaa_5$, $Xaa_6$, $Xaa_7$, and $Xaa_8$-$Xaa_{11}$ are as hereinbefore defined, as well as regioisomers, stereoisomers, and pharmaceutically- or cosmetically-acceptable salts thereof.

Compounds of the invention that may be mentioned include those in which:

$Xaa_1$ represents Ala or Lys-Ala-; and/or $Xaa_{12}$ represents DOPA or dopamine.

In this respect, further compounds of the invention that may be mentioned include those of the amino acid sequence:

Ala-Lys-Pro-Ser-Tyr-Xaa-Thr-Tyr-Xaa-Lys-Xaa (SEQ ID No: 38), where Xaa at position 11 is DOPA as defined herein and where Xaa at positions 6 and 9 are Hyp as defined herein;

Ala-Lys-Pro-Ser-Tyr-Xaa-Thr-Tyr-Xaa-Lys-Dopamine (SEQ ID No: 39), where Xaa at positions 6 and 9 are Hyp as defined herein;

Ala-Lys-Pro-Ser-Tyr-Xaa-Xaa-Thr-Tyr-Lys-Dopamine (SEQ ID No: 40), where Xaa at positions 6 and 7 are Hyp as defined herein;

Ala-Lys-Pro-Ser-Tyr-Xaa-Xaa-Thr-Tyr-Lys-Xaa (SEQ ID No: 41), where Xaa at position 11 is DOPA as defined herein and where Xaa at positions 6 and 7 are Hyp as defined herein;

Ala-Lys-Pro-Ser-Tyr-Xaa-Xaa-Thr-Xaa-Lys-Xaa (SEQ ID No: 42), where Xaa at positions 9 and 11 is DOPA as defined herein and where Xaa at positions 6 and 7 are Hyp as defined herein;

Ala-Lys-Pro-Ser-Xaa-Xaa-Xaa-Thr-Tyr-Lys-Xaa (SEQ ID No: 43), where Xaa at positions 5 and 11 is DOPA as defined herein and where Xaa at positions 6 and 7 are Hyp as defined herein;

Ala-Lys-Pro-Ser-Xaa-Xaa-Xaa-Thr-Xaa-Lys-Xaa (SEQ ID No: 44), where Xaa at positions 5, 9, and 11 is DOPA as defined herein and where Xaa at positions 6 and 7 are Hyp as defined herein;

Ala-Lys-Pro-Ser-Tyr-Xaa-Xaa-Thr-Xaa-Lys-Dopamine (SEQ ID No: 45), where Xaa at position 9 is DOPA as defined herein and where Xaa at positions 6 and 7 are Hyp as defined herein;

Ala-Lys-Pro-Ser-Xaa-Xaa-Xaa-Thr-Tyr-Lys-Dopamine (SEQ ID No: 46), where Xaa at position 5 is DOPA as defined herein and where Xaa at positions 6 and 7 are Hyp as defined herein;

Ala-Lys-Pro-Ser-Xaa-Xaa-Xaa-Thr-Xaa-Lys-Dopamine (SEQ ID No: 47), where Xaa at positions 5 and 9 is DOPA as defined herein and where Xaa at positions 6 and 7 are Hyp as defined herein;

Ala-Lys-Pro-Ser-Tyr-Xaa-Thr-Xaa-Xaa-Lys-Xaa (SEQ ID No: 48), where Xaa at positions 8 and 11 is DOPA as defined herein and where Xaa at positions 6 and 9 are Hyp as defined herein;

Ala-Lys-Pro-Ser-Xaa-Xaa-Thr-Tyr-Xaa-Lys-Xaa (SEQ ID No: 49), where Xaa at positions 5 and 11 is DOPA as defined herein and where Xaa at positions 6 and 9 are Hyp as defined herein;

Ala-Lys-Pro-Ser-Xaa-Xaa-Thr-Xaa-Xaa-Lys-Xaa (SEQ ID No: 50), where Xaa at positions 5, 8, and 11 is DOPA as defined herein and where Xaa at positions 6 and 9 are Hyp as defined herein;

Ala-Lys-Pro-Ser-Tyr-Xaa-Thr-Xaa-Xaa-Lys-Dopamine (SEQ ID No: 51), where Xaa at position 8 is DOPA as defined herein and where Xaa at positions 6 and 9 are Hyp as defined herein;

Ala-Lys-Pro-Ser-Xaa-Xaa-Thr-Tyr-Xaa-Lys-Dopamine (SEQ ID No: 52), where Xaa at position 5 is DOPA as defined herein and where Xaa at positions 6 and 9 are Hyp as defined herein;

Ala-Lys-Pro-Ser-Xaa-Xaa-Thr-Xaa-Xaa-Lys-Dopamine (SEQ ID No: 53), where Xaa at positions 5 and 8 is DOPA as defined herein and where Xaa at positions 6 and 9 are Hyp as defined herein;

Lys-Ala-Lys-Pro-Ser-Tyr-Xaa-Xaa-Thr-Xaa (SEQ ID No: 54), where Xaa at position 10 is DOPA as defined herein and where Xaa at positions 7 and 8 are Hyp as defined herein;

Lys-Ala-Lys-Pro-Ser-Tyr-Xaa-Xaa-Thr-Dopamine (SEQ ID No: 55), where Xaa at positions 7 and 8 are Hyp as defined herein;

Lys-Ala-Lys-Xaa-Ser-Tyr-Xaa-Xaa-Thr-Xaa (SEQ ID No: 56), where Xaa at position 10 is DOPA as defined herein and where Xaa at positions 4, 7, and 8 are Hyp as defined herein;

Lys-Ala-Lys-Pro-Ser-Xaa-Xaa-Xaa-Thr-Xaa (SEQ ID No: 57), where Xaa at positions 6 and 10 is DOPA as defined herein and where Xaa at positions 7 and 8 are Hyp as defined herein;

Lys-Ala-Lys-Pro-Ser-Xaa-Xaa-Xaa-Thr-Dopamine (SEQ ID No: 58, where Xaa at position 6 is DOPA as defined herein and where Xaa at positions 7 and 8 are Hyp as defined herein; and Lys-Ala-Lys-Xaa-Ser-Xaa-Xaa-Xaa-Thr-Xaa (SEQ ID No: 59), where Xaa at positions 6 and 10 is DOPA as defined herein and where Xaa at positions 4, 7, and 8 are Hyp as defined herein.

Particular compounds of the invention that may be mentioned from the list above include those of the amino acid sequence:

Ala-Lys-Pro-Ser-Tyr-Xaa-Thr-Tyr-Xaa-Lys-Xaa (SEQ ID No: 38), where Xaa at position 11 is DOPA as defined herein and where Xaa at positions 6 and 9 are Hyp as defined herein;

Ala-Lys-Pro-Ser-Tyr-Xaa-Thr-Tyr-Xaa-Lys-Dopamine (SEQ ID No: 39), where Xaa at positions 6 and 9 are Hyp as defined herein;

Lys-Ala-Lys-Pro-Ser-Tyr-Xaa-Xaa-Thr-Xaa (SEQ ID No: 54), where Xaa at position 10 is DOPA as defined herein and where Xaa at positions 7 and 8 are Hyp as defined herein; and Lys-Ala-Lys-Pro-Ser-Tyr-Xaa-Xaa-Thr-Dopamine (SEQ ID No: 55), where Xaa at positions 7 and 8 are Hyp as defined herein.

Further, compounds of the invention that may be mentioned include those in which $Xaa_6$ represents Hyp or, particularly, Pro.

For such compounds of the invention, $Xaa_7$ to $Xaa_{11}$ may represent a 4 amino acid sequence selected from the group -Pro-$Xaa_8$-$Xaa_9$-Lys- (SEQ ID NO: 75), -Hyp-$Xaa_8$-$Xaa_9$-Lys- (SEQ ID NO: 76) and -Thr-$Xaa_8$-$Xaa_9$-Lys- (SEQ ID NO: 77), wherein $Xaa_8$ and $Xaa_9$ are each independently selected from the group Pro, Ala, Hyp, Thr, DOPA and Tyr.

When $Xaa_7$ to $Xaa_{11}$ represents a 4 amino acid sequence of the formula -Hyp-$Xaa_8$-$Xaa_9$-Lys- (SEQ ID NO: 76) or -Thr-$Xaa_8$-$Xaa_9$-Lys- (SEQ ID NO: 77), $Xaa_8$ and $Xaa_9$ are as hereinbefore defined or $Xaa_8$ and/or $Xaa_9$ may represents Pro, such that the amino acid sequence defined by Y is selected from the group -Thr-Tyr-Pro-Lys- (SEQ ID NO: 80) and -Thr-DOPA-Pro-Lys- (SEQ ID NO: 81).

When Y represents a 4 amino acid sequence of the formula -Pro-Xaa-$Xaa_9$-Lys- (SEQ ID NO: 75), preferred compounds of the invention include those in which the amino acid sequence defined by Y is selected from the group -Pro-Thr-DOPA-Lys- (SEQ ID NO: 78) and -Pro-Thr-Tyr-Lys- (SEQ ID NO: 79).

In all such compounds:

$Xaa_1$ preferably represents Ala;

$Xaa_3$ preferably represents Pro; and/or $Xaa_{12}$ is preferably absent.

In this respect, further compounds of the invention that may be mentioned include those of the amino acid sequence:

Ala-Lys-Pro-Ser-Tyr-Pro-Pro-Thr-Xaa-Lys (SEQ ID No: 60), where Xaa at position 9 is DOPA as defined herein;

Ala-Lys-Pro-Ser-Xaa-Pro-Pro-Thr-Tyr-Lys (SEQ ID No: 61), where Xaa at position 5 is DOPA as defined herein;

Ala-Lys-Pro-Ser-Xaa-Pro-Pro-Thr-Xaa-Lys (SEQ ID No: 62), where Xaa at positions 5 and 9 is DOPA as defined herein;

Ala-Lys-Pro-Ser-Tyr-Pro-Thr-Tyr-Pro-Lys (SEQ ID No: 63);

Ala-Lys-Pro-Ser-Tyr-Pro-Thr-Xaa-Pro-Lys (SEQ ID No: 64), where Xaa at position 8 is DOPA as defined herein;

Ala-Lys-Pro-Ser-Xaa-Pro-Thr-Tyr-Pro-Lys (SEQ ID No: 65), where Xaa at position 5 is DOPA as defined herein;

Ala-Lys-Pro-Ser-Xaa-Pro-Thr-Xaa-Pro-Lys (SEQ ID No: 66), where Xaa at position 5 and 8 is DOPA as defined herein;

Ala-Lys-Pro-Ser-Tyr-Pro-Xaa-Thr-Tyr-Lys (SEQ ID No: 67), where Xaa at position 7 is Hyp as defined herein;

Ala-Lys-Pro-Ser-Tyr-Pro-Xaa-Thr-Xaa-Lys (SEQ ID No: 68), where Xaa at position 9 is DOPA as defined herein and where Xaa at position 7 is Hyp as defined herein;

Ala-Lys-Pro-Ser-Xaa-Pro-Xaa-Thr-Tyr-Lys (SEQ ID No: 69), where Xaa at position 5 is DOPA as defined herein and where Xaa at position 7 is Hyp as defined herein;

Ala-Lys-Pro-Ser-Xaa-Pro-Xaa-Thr-Xaa-Lys (SEQ ID No: 70), where Xaa at positions 5 and 9 is DOPA as defined herein and where Xaa at position 7 is Hyp as defined herein;

Ala-Lys-Pro-Ser-Tyr-Xaa-Pro-Thr-Tyr-Lys (SEQ ID No: 71), where Xaa at position 6 is Hyp as defined herein;

Ala-Lys-Pro-Ser-Tyr-Xaa-Pro-Thr-Xaa-Lys (SEQ ID No: 72), where Xaa at position 9 is DOPA as defined herein and where Xaa at position 6 is Hyp as defined herein;

Ala-Lys-Pro-Ser-Xaa-Xaa-Pro-Thr-Tyr-Lys (SEQ ID No: 73), where Xaa at position 5 is DOPA as defined herein and where Xaa at position 6 is Hyp as defined herein; and Ala-Lys-Pro-Ser-Xaa-Xaa-Pro-Thr-Xaa-Lys (SEQ ID No: 74), where Xaa at positions 5 and 9 is DOPA as defined herein and where Xaa at position 6 is Hyp as defined herein.

As used herein, Pro represents proline, Ala represents alanine, Ser represents serine, Tyr represents tyrosine, Hyp represents hydroxyproline (including 3-hydroxyproline (3Hyp) and 4-hydroxyproline (4Hyp)), diHyp represents dihydroxyproline (including 3,4-dihydroxyproline (3,4diHyp), 3,5-dihydroxyproline (3,5diHyp) and 4,5-dihydroxyproline (4,5diHyp)), Thr represents threonine, Lys represents lysine, Ala represents alanine and DOPA represents 3,4-dihydroxyphenylalanine. 3,4-Dihydrocinnamic acid (HCA) residues are essentially DOPA residues but without the —$NH_2$ group in the 2- or α-carbon position relative to the carboxylic acid that is attached to the N-terminal amino acid (whether Lys or Ala).

Compounds of the invention, whether in the form of salts or otherwise, include regioisomers within amino acids of the peptides (for example diHyp, Hyp and Tyr moieties), as well as mixtures of such regioisomers. For example, included within the definition of Tyr are, not only tyrosine (4-hydroxyphenylalanine), but also 2- and 3-hydroxyphenylalanine. Included within the definition of Hyp are 4-hydroxyproline (4Hyp), 3-hydroxyproline (3Hyp) and 5-hydroxyproline (5Hyp). It is more preferred that Hyp residues are 4-hydroxyproline. Similarly, included within the definition of diHyp are 3,4-dihydroxyproline (3,4diHyp), 3,5-dihydroxyproline (3,5diHyp) and 4,5-dihydroxyproline (4,5diHyp). It is more preferred that diHyp residues are 3,4-dihydroxyproline (3,4diHyp).

Also, in addition to the standard central carbon atom of the amino acids in the compounds of the invention (which are normally but not exclusively in the L-configuration), certain amino acids in the sequence comprise further chiral carbon atoms. All such stereoisomers and mixtures (including racemic mixtures) thereof are included within the scope of the invention. In respect, included within the definition of Hyp are trans-4-hydroxy-L-proline, cis-4-hydroxy-L-proline, trans-3-hydroxy-L-proline, cis-3-hydroxy-L-proline, trans-5-hydroxy-L-proline and cis-5-hydroxy-L-proline, however we prefer that the Hyp that is employed in compounds of the invention is 4-hydroxy-L-proline. Similarly, corresponding definitions may be applied to diHyp, in which the two hydroxy groups can also be cis or trans relative to each other. In any event, individual enantiomers of compounds of the invention are included within the scope of the invention.

Compounds of the invention may be in the form of salts. Salts that may be mentioned include pharmaceutically-acceptable and/or cosmetically-acceptable salts, such as pharmaceutically- and/or cosmetically-acceptable acid addition salts and base addition salts. Such salts may be formed by conventional means, for example by reaction of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of the compound of the invention in the form of a salt with another counter-ion, for example using a suitable ion exchange resin.

Preferred salts include, for example, acetate, hydrochloride, bisulfate, maleate, mesylate, tosylate, alkaline earth metal salts, such as calcium and magnesium, or alkali metal salts, such as sodium and potassium salts. Most preferably, compounds of the invention may be in the form of acetate salts.

Compounds of the invention may be prepared by way of conventional techniques, for example by way of standard amino acid coupling techniques, using standard coupling reagents and solvents, for example as described hereinafter. Compounds of the invention may be synthesised from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, 3rd edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in '*Protective Groups in Organic Synthesis',* 5th edition, T. W. Greene & P. G. M. Wutz, Wiley-Interscience (2014), the contents of which are incorporated herein by reference.

Compounds of the invention are useful as human and animal medicine. They are therefore indicated as pharmaceuticals (and/or in veterinary science), although they may also be used as cosmetics and/or as part of a medical device.

Compounds of the invention may possess pharmacological activity as such, certain pharmaceutically-acceptable (e.g. 'protected') derivatives of compounds of the invention may exist or may be prepared which may not possess such activity, but which may be administered and thereafter be metabolised or chemically transformed to form compounds of the invention. Such compounds (which may possess some pharmacological activity, provided that such activity is appreciably lower than that of the active compounds to which they are metabolised/transformed) may therefore be described as 'prodrugs' of compounds of the invention.

As used herein, references to prodrugs will include compounds that form a compound of the invention, in an experimentally-detectable amount, within a predetermined time, following administration. All prodrugs of the compounds of the invention are included within the scope of the invention.

Compounds of the invention are particularly useful in the treatment of inflammation.

The term 'treatment of inflammation' includes the treatment of inflammation in any organ of the body (including soft tissue, joints, nerves, the vascular system, internal organs, especially mucosal surfaces, and particularly the skin), irrespective of the cause, and also includes all such inflammatory disorders or conditions, and/or disorders or conditions characterized by inflammation (e.g. as a symptom).

Inflammatory disorders and/or conditions may be (and are typically) characterized by activation of immune defence mechanisms, resulting in an effect that is more harmful than beneficial to the host. Such conditions are generally associated with varying degrees of tissue redness or hyperemia, swelling, edema, hyperthermia, pain (including aching), exudation of body fluids, itching (pruritis), cell death and tissue destruction, cell proliferation, and/or loss of function.

Inflammatory conditions that may be mentioned include arteritis, diabetes mellitus, metabolic syndrome, rosacea, asthma and allergy, ankylosing spondylitis, chronic obstructive pulmonary disease, gouty arthritis, inflammatory bowel disease (such as Crohn's disease and ulcerative colitis), multiple sclerosis, osteoarthritis, pancreatitis, prostatitis, psoriatic arthritis, rheumatoid arthritis, tendinitis, bursitis, Sjögren's syndrome, systemic lupus erythematosus, uveitis, urticaria, vasculitis, mastocytosis, diabetic vascular complications, migraine, atherosclerosis and associated cardiovascular disorders. A disease state characterised by inflammation that may be mentioned is chronic obstructive pulmonary disease (COPD). A further disease state characterised by inflammation that may be mentioned is inflammatory bowel diseases including Crohn's disease and, especially, ulcerative colitis. Other disease states characterized by inflammation that may be mentioned are gynaecological diseases, such as cervicitis, vaginitis (e.g. radiation vaginitis) and colpitis. Diseases that affect the gastrointestinal tract, such as gastrohelcosis (e.g. gastritis, gastric ulcer, gastric cancer and other stomach mucosa diseases) as well as gastroesophageal reflux disease (GERD), constipation, and gastritis, inflammation associated with cancers and infections (e.g. viral infections, such as the common cold or influenza).

Inflammatory conditions that may be more especially mentioned include inflammations of the skin or mucosa (including the oral, nasal, ocular, vaginal, cervical and/or anorectal mucosae, more particularly the oral or nasal mucosae), such as inflammation resulting from infections (such as viral and/or bacterial infections), or allergic/atopic conditions (such as rhinitis (e.g. allergic rhinitis), pharyngitis, periodontitis, gingivitis, xerophthalmia, conjunctivitis (e.g. allergic conjunctivitis), dermatitis, urticaria (hives) and food allergy); and other inflammatory conditions, such as herpes, drug eruptions, polymorphous light eruptions, sunburn, early manifestations of skin cancers (erythema-like skin lesions), pathological hair loss (including following skin grafting), chemo rash, psoriasis, erythema multiforme, folliculitis, eczema and external otitis. A disease state that may be mentioned is polymorphous light eruptions.

More particularly, compounds may be used to treat certain conditions characterized by inflammation, and/or with which inflammation is associated. Such conditions may include wounds (including abrasions (scratches), incisions (including operative incisions), lacerations, punctures, avulsions, bruising and scarring), and burns (including inflammation resulting from surgery following burns, such as skin grafting) and other conditions, such as hemorrhoids. Wounds may be acute or chronic, and/or may result from one or more inflammatory disorders as defined herein.

Wounds of the skin or mucosa may arise from internal or external physical injury to the membrane surface, or may be caused by (i.e. be a symptom of) an underlying physiological disorder.

Physical (e.g. 'open') wounds may be caused by sharp objects (cuts, incisions, punctures) or blunt objects/mechanical forces (lacerations, abrasions, avulsions), physical blows (bruises), heat or chemicals (burns and blisters), UV light (sunburn), cold (chilblains or frostbite). Wounds may be superficial (damage only to the epidermis and/or dermis) or may be full thickness wounds (damage below the epidermis and/or dermis). In serious cases, subcutaneous and/or submucosal tissues, such as muscles, bones, joints, and even internal organs, may be damaged.

Compounds of the invention may be used to relieve the pain (including aching) associated with inflammation and/or wounding. In particular, compounds of the invention may be used to relieve procedural pain and/or non-procedural pain. The skilled person will understand that the term 'procedural pain' (i.e. operation pain) refers to acute pain that is associated with medical investigations and treatments conducted for the purpose of healthcare. The term 'non-procedural' refers to general pain that is associated with inflammation and/or wounding (e.g. pain associated with dental ulcers, burns and/or scars), and is not a consequence of a particular medical intervention.

Compounds of the invention may be used to treat not only the inflammation, pain (including aching) and/or pruritis (itching) associated with the wound itself and the healing process, but also to prevent the exudation of body fluids from wounds, the risk of infection, and the prevention of physiological reactions that result from inflammation and/or wound healing processes, such as scarring and melanin pigmentation.

Scarring is a consequence of inflammation and/or wound healing and is a general term for the formation of fibrotic tissue that is a consequence of such inflammation/healing.

Compounds of the invention may also be useful in the suppression of the production of melanin pigmentation, which may or may not result from inflammation and/or wound healing. Compounds of the invention may also be useful in the suppression of disorders associated with melanin pigmentation, such as chloasma, freckles, melanosis, malar rash and other chromatosis, skin cancers with melanoma, and chromatosis that is caused by exposure to the sun or skin diseases like acne.

Wounds may also arise as a consequence of (e.g. inflammatory) diseases or disorders. Such wounds may include blistering and/or ulcers of the skin and mucosa. These are common conditions that are often long-lasting and difficult to treat. Skin tissues can often be damaged, removed, liquefied, infected and/or necrotic. Ulcers can lead to secondary consequences to health particularly if they become infected, are hard to heal and are costly to treat. They can also cause significant psychological stress and economic loss to patients, affecting both general well-being and quality of life.

In the alternative, inflammatory skin conditions or diseases in which compounds of the invention find particular utility include psoriasis, acne, eczema and dermatitis, especially allergic/atopic dermatitis, as well as in the treatment of mucosal inflammation as characterized by rhinitis, especially allergic rhinitis, hemorrhoids, chronic obstructive pulmonary disease and ulcerative colitis, for example.

Psoriasis is a chronic, inflammatory skin disease with a tendency to recur (some patients never heal during their entire life). Clinical manifestations of psoriasis mainly include erythema and scales. It can occur over the whole body, but is more commonly observed on the scalp and limbs.

Acne is a follicular (pilosebaceous unit) chronic, inflammatory skin disease, the occurrence of which is closely related to main factors like hypersteatosis, blocked pilosebaceous ducts (including closed and open comedones), bacterial infection and inflammatory reactions, that tends to occur during youth, characterized by multiform skin lesions on the face. The term acne thus includes regular acne and acne rosacea (i.e. copper nose).

Eczema is a skin inflammatory reaction with strong itching caused by a variety of internal and external factors. It has three phases, acute, sub-acute, and chronic. In the acute phase, there is a tendency for the production of exudates, while the chronic phase includes infiltration and hypertrophy. Skin lesions are often itchy and recur easily.

Dermatitis is a common skin disease characterized by coarseness, redness, itching, eczema, and dryness. Small lumps, refractory ulcers, and pigmented spots caused by dermatitis may, if not treated promptly, develop to basal cell carcinoma, squamous cell carcinoma, and malignant melanoma. Dermatitis may be caused by various internal and external infectious or non-infectious factors, including substances (contact dermatitis) or allergy (allergic/atopic dermatitis). Also included is seborrheic dermatitis (seborrheic eczema) and all forms of steroid-dependent dermatitis (including light-sensitive seborrheic, perioral dermatitis, rosacea-like dermatitis, steroid-rosacea, steroid-induced rosacea, iatrosacea, steroid dermatitis resembling rosacea, topical corticosteroid-induced rosacea-like dermatitis and, more particularly, facial corticosteroid addictive dermatitis (FCAD) or facial corticosteroid-dependent dermatitis (FCDD), as characterized by flushing, erythema, telangiectasia, atrophy, papules and/or pustules in the facial area after long-term treatment with (including uncontrolled use, abuse or misuse of) topical corticosteroids; see, for example, Xiao et al., *J. Dermatol.,* 2015, 42, 697-702 and Lu et al., *Clin. Exp. Dermatol.,* 2009, 35, 618-621.

Rhinitis is irritation and inflammation of the mucous membrane inside the nose. Common symptoms of rhinitis include a stuffy nose, runny nose, sneezing and post-nasal drip. The most common kind of rhinitis is allergic rhinitis, caused by an allergen, such as pollen, dust, mould, or flakes of skin from certain animals. It has been surprisingly found that patients with allergic rhinitis who were treated with compounds of the invention experienced relief of eye itchiness, even when compounds of the invention were administered nasally (i.e. to the nasal mucosa).

Hemorrhoids are swellings caused by inflammation of the hemorrhoidal blood vessels found inside or around the rectum and the anus. Symptoms include bleeding (i.e. wounding) after the passage of a stool, prolapse of the hemorrhoid, mucus discharge and itchiness, soreness, redness and swelling in the area of the anus. Hemorrhoids are believed to be a consequence of an increase of pressure in the abdomen, for example, as a result of constipation or diarrhea.

Chronic obstructive pulmonary disease (COPD) is the name for a group of lung conditions that cause breathing difficulties, including emphysema (damage to the alveoli) and chronic bronchitis (long-term inflammation of the airways). COPD occurs when the lungs become inflamed, damaged and narrowed. The damage to the lungs is usually irreversible and results in an impairment of the flow of air into and out of the lungs. Symptoms of COPD include breathlessness, productive cough, frequent chest infections and persistent wheezing. The most common cause of the disease is smoking, although other risk factors include high levels of air pollution and occupational exposure to dust, chemicals and fumes.

Compounds of the invention may have positive effects in mitigating erythema, redness and swelling, edema, blisters, and bullous pemphigoid caused by various conditions including those mentioned generally and specifically herein, and may inhibit exudation of subcutaneous tissue fluid, and suppressing itching and pain caused by such inflammatory conditions.

Other inflammatory conditions that may be mentioned include:

(a) Mucosal inflammation, such as oral mucositis, aphthous ulcers, otitis media, laryngitis, tracheitis, esophagitis, gastritis, enteritis and enterocolitis (including bacillary dysentery, chronic amoebic dysentery, schistosomiasis, nonspecific ulcerative colitis and regional enteritis), cervicitis and endocervicitis, endometritis, inflammation caused by inhalation injury and the like, as well as mucosal inflammation associated with cancers, and infections (e.g. viral infections, such as the common cold or influenza), that affect mucosal surfaces, such as those in the oral cavity, the nasopharynx, the ear, the throat, the trachea, the gastrointestinal tract, the cervix, etc.

(b) Orthopedic inflammation associated with, for example bone fractures, pyogenic infection of bones and joints, inflammation caused by rheumatic bone diseases, as well as pyogenic osteomyelitis (acute, chronic, localized, sclerotic, post-traumatic), pyogenic arthritis; bone tumors (osteoma, osteoid osteoma, chondroma), bone cysts, osteoclastoma, primary bone sarcoma (osteosarcoma, chondrosarcoma, osteofibrosarcoma, Ewing's sarcoma, non-Hodgkin's lymphoma, myeloma, chordoma), metastatic bone tumors, tumor-like lesions of bone (bone cyst, aneurysmal bone cyst, eosinophilic granuloma, fibrous dysplasia); and rheumatic arthritis.

(c) Nerve inflammation, such as peripheral polyneuritis, facial neuritis, peripheral neuritis, subcutaneous neuritis, ulnar neuritis, intercostal neuritis, etc.

(d) Subcutaneous and submucosal soft tissue inflammation, such as myositis, ligamentitis, tendonitis, panniculitis capsulitis, lymphadenitis, bubonadentitis, tonsillitis, synovitis, fasciitis, and soft tissue inflammation caused by injuries, contusion or laceration of muscles, ligaments, fascia, tendons, membrana synovialis, fat, articular capsules, and lymphoid tissue.

(e) Vascular inflammation, such as allergic leukocytoclastic vasculitis, allergic cutaneous vasculitis, polyarteritis nodosa, thrombotic vasculitis, granulomatous vasculitis, lymphocytic vasculitis, vasculitis with abnormalities in blood composition, and rheumatic vasculitis, as well as vascular inflammation associated with vascular cancers caused by allergic leukocytoclastic vasculitis, polyarteritis nodosa, thrombotic vasculitis, granulomatous vasculitis, lymphocytic vasculitis, vasculitis with abnormalities in blood composition, and rheumatic vasculitis.

(f) Inflammation of the internal organs, such as the heart, stomach, intestine, lung, liver, spleen, kidney, pancreas, bladder, ovary, and prostate, including but not limited to pericarditis, myocarditis, endocarditis, pneumonia, hepatitis, splenitis, nephritis pancreatitis, cystitis, oophoritis, prostatitis and treatment of gastric ulcer.

(g) Inflammation of the eye and surrounding area, such as conjunctivitis, keratitis (e.g. acute epithelial keratitis, nummular keratitis, interstitial keratitis, disciform keratitis, neurotrophic keratitis, mucous plaque keratitis, herpes simplex keratitis, herpes zoster keratitis, bacterial keratitis, fungal keratitis acanthamoebic keratitis, onchocercal keratitis, superficial punctate keratitis, ulcerative keratitis, exposure keratitis photokeratitis and contact lens acute red eye), optic neuritis, etc.

(h) Inflammation of the gums and the oral cavity, such as periodontitis, gingivitis, dental ulcers, etc.

(i) Inflammation associated with rheumatism, such as rheumatic vasculitis, rheumatoid arthritis, rheumatic bone diseases, ankylosing spondylitis, bursitis, Crohn's disease, gout, infectious arthritis, juvenile idiopathic arthritis, osteoarthritis, osteoporosis, polymyalgia rheumatica, polymyositis, psoriatic arthritis, scleroderma, Sjögren's syndrome, spondyloarthropathies, systemic lupus erythematosus, tendinitis, etc.

Compounds of the invention may also be used in the treatment of certain specific diseases of the digestive system, such as gastroesophageal reflux disease (GERD), which may be characterized by an acidic taste in the mouth, regurgitation, heartburn, pain with swallowing and/or sore throat, increased salivation (water brash), nausea, chest pain, and coughing. GERD may cause injury of the esophagus, including reflux esophagitis (i.e. inflammation of the esophageal epithelium which may cause ulceration at or around the junction of the stomach and esophagus), esophageal strictures (i.e. the persistent narrowing of the esophagus caused by reflux-induced inflammation), Barrett's esophagus (i.e. intestinal metaplasia (i.e. changes of epithelial cells from squamous to intestinal columnar epithelium of the distal esophagus) and/or esophageal adenocarcinoma (a form of cancer)).

Compounds of the invention may also be used in the treatment of certain specific diseases of the respiratory system, such as pulmonary cystic fibrosis, usual interstitial pneumonia, allergic pneumonia, asbestosis, emphysema, pulmonary heart disease, pulmonary embolism, etc. A specific disease state that may be mentioned in idiopathic pulmonary fibrosis (IPF).

IPF is a diffuse and fatal pulmonary interstitial disease with pathological features including alveolar epithelial damage, massive proliferation of lung fibroblasts, excessive deposition of extracellular matrix, ultimately leading to irreversible lung tissue damage. In the latter stages of the disease, subjects with IPF experience respiratory failure and death. It has been found that compounds of the invention may find utility in the treatment of IPF and/or alleviation of the symptoms associated with the disease.

Compounds of the invention are particularly useful in the treatment of the following lung and/or fibrotic conditions (whether otherwise mentioned herein or not): lung fibrosis, renal fibrosis, liver fibrosis, silicosis, acute bronchitis, chronic bronchitis, tracheobronchitis, bronchial asthma, status asthmatics, bronchiectasis, upper respiratory tract infections (including the common cold and influenza), allergic airway inflammation, bacterial pneumonia, viral pneumonia, mycoplasma pneumonia, reckettsia, radiation pneumonia, pneumococcal (including staphylococcal, streptococcal and gram-negative bacillus) pneumonia, pulmonary candidiasis (including aspergillosis, mucormycosis, histoplasmosis, actinomycosis and nocardiosis), pulmonary mycosis, cryptococcosis, lung abscesses, anaphylactic pneumonia, extrinsic allergic alveolitis, pulmonary eosinophilia (including Loeffler's syndrome and eosinophilosis), obstructive pulmonary emphysema, pulmonary edema, pulmonary tuberculosis, respiratory alkalosis/acidosis, acute lung injury, interstitial lung disease, empyema, lung fibroma and cor pulmonale.

Particular mucosal disorders and disease in which compounds of the invention find utility include anorectal diseases, such as diarrhea, hemorrhoids, abscesses, fistula, fissures, anal itching, anal sinusitis, warts and rectal prolapse; inflammatory bowel disease, including Crohn's disease and, particularly, ulcerative colitis; gynaecological diseases, such as cervicitis, vaginitis, pelvic pain and disorders; and dental diseases, such as paradentitis, for example.

Compounds of the invention may further possess an antioxidation effect, by increasing SOD (superoxide dismutase) production and reducing lipid oxidation. Compounds of the invention may therefore be considered to have antioxidant properties.

Compounds of the invention may also possess antipyretic properties that allow for the treatment of a fever and/or alleviate the symptoms thereof; for example, by reducing a subject's body temperature, which results in a reduction of fever. Compounds of the invention and formulations including them may therefore be considered to be antipyretics.

According to a further aspect of the invention there is provided a method of treatment of inflammation, of an inflammatory disorder, and/or of a disorder/condition characterised by inflammation (for example as a symptom), which method comprises the administration of a compound of the invention or a salt thereof to a patient in need of such treatment.

For the avoidance of doubt, in the context of the present invention, the terms 'treatment', 'therapy' and 'therapy method' include the therapeutic, or palliative, treatment of patients in need of, as well as the prophylactic treatment and/or diagnosis of patients which are susceptible to, inflammation and/or inflammatory disorders.

Compounds of the invention may further possess antiviral properties that may allow for the treatment of a viral infection per se, that is treatment of a viral infection, or a viral disease, by interfering with the replication of the virus within a host, as opposed to the treatment of any symptoms of any viral infection or disease, such as pain and/or inflammation. Such antiviral properties may also allow for the prevention of the onset of such an infection or disease, the protection of cells in a host from (e.g. further) viral infection, prevention or arrest of the spread of viral infection or disease (within a single host, or from one host to a new host), or for the prevention of reactivation of a virus after latency in a host.

According to a further aspect of the invention there is provided a method of treatment of a viral infection, which method comprises the administration of a compound of the invention or a salt thereof to a patient in need of such treatment.

Viral infections that may be mentioned include those caused by viruses in the following families: adenoviridae (e.g. adenovirus), papillomaviridae (e.g. human papillomavirus), polyomaviridae (e.g. BK virus; JC virus), herpesviridae (e.g. herpes simplex, type 1; herpes simplex, type 2; varicella-zoster virus; Epstein-Barr virus; human cytomegalovirus; human herpes virus, type 8), poxviridae (e.g. smallpox), hepadnaviridae (e.g. hepatitis B virus), parvoviridae (e.g. parvovirus B19), astroviridae (e.g. human astrovirus), caliciviridae (e.g. norovirus; Norwalk virus), picornaviridae (e.g. coxsackievirus, hepatitis A virus; poliovirus; rhinovirus), coronoviridae (e.g. severe acute respiratory syndrome virus), flaviviridae (e.g. hepatitis C virus; yellow fever virus; dengue virus; West Nile virus; tick-borne encephalitis virus), retroviridae (e.g. human immunodeficiency virus; HIV), togaviridae (e.g. rubella virus), arenaviridae (e.g. Lassa virus), bunyaviridae (e.g. hantavirus; Crimean-Congo hemorrhagic fever virus; Hantaan virus), filoviridae (e.g. Ebola virus; Marburg virus; Ravn virus), orthomyxoviridae (e.g. influenza viruses, including influenza A virus (e.g. H1N1 and H3N2 viruses), influenza B virus or influenza C virus), paramyxoviridae (e.g. measles virus; mumps virus; parainfluenza virus, respiratory syncytial virus), rhabdoviridae (e.g. rabies virus), hepeviridae (e.g. hepatitis E virus), reoviridae (e.g. rotavirus; orbivirus; coltivirus; Banna virus), as well as viruses not assigned to families, such as hepatitis D virus.

Viruses that may be more specifically mentioned include herpes simplex, type 1 and herpes simplex, type 2 viruses, human papillomavirus, influenza virus and parainfluenza virus.

Compounds of the invention may further possess antibacterial and/or bacteriostatic properties that may allow for the treatment of a bacterial infection per se, that is treatment of a bacterial infection, or a bacterial disease, by interfering with bacterial growth or proliferation in a host, as opposed to the treatment of any symptoms of any bacterial infection or disease, such as pain and/or inflammation. Compounds of the invention may therefore be considered to be bacteriocides and/or, preferably, bacteriostatic agents.

Such antibacterial properties may also allow for the prevention of the onset of such an infection or disease, the protection of cells in a host from (e.g. further) bacterial infection, prevention or arrest of the spread of bacterial infection or disease (within a single host, or from one host to a new host), or for the prevention of reactivation of a bacterium after latency in a host.

According to a further aspect of the invention there is provided a method of treatment of a bacterial infection, which method comprises the administration of a compound of the invention or a salt thereof to a patient in need of such treatment.

As disclosed herein, compounds of the invention may further possess anticancer properties that may allow for the treatment of a cancer per se, that is treatment of a cancer by interfering with the cancer as opposed to the treatment of any symptoms of the cancer, such as pain and/or inflammation. Such anticancer properties may also include the prevention of the onset of such a disease e.g. by treating inflammation and thereby preventing such onset.

According to another aspect of the invention, there is provided a method of treatment of cancer, which method comprises the administration of a compound of the invention or a salt thereof to a patient in need of such treatment.

Particular cancers that may be mentioned include oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, skin cancer and the like caused by oral mucositis, rhinitis, otitis media, conjunctivitis, pharyngitis, laryngitis, tracheitis, esophagitis, gastritis, enterocolitis, cervicitis, endometritis, erythema-like skin lesions and the like. A particular skin cancer that may be mentioned is basal cell carcinoma.

'Patients' include reptilian, avian and, preferably, mammalian (particularly human) patients.

In accordance with the invention, compounds of the invention are preferably administered locally or systemically, for example orally, intravenously or intraarterially (including by intravascular and other perivascular devices/dosage forms (e.g. stents)), intramuscularly, cutaneously, subcutaneously, transmucosally (e.g. sublingually or buccally), rectally, intravaginally, intradermally, transdermally, nasally, pulmonarily (e.g. tracheally or bronchially), preferably topically, or by any other parenteral route, in the form of a pharmaceutical preparation comprising the compound(s) in pharmaceutically acceptable dosage form(s).

Administration by inhalation (e.g. nasally) is particularly useful when the condition to be treated is rhinitis or inflammation resulting from viral infections of the airways (e.g. upper respiratory tract infections, such as the common cold and influenza).

Pulmonary administration is particularly useful when the condition to be treated is COPD or IPF. Topical forms of administration may be enhanced by creating a spray comprising compounds of the invention, e.g. by using a powder aerosol or by way of an aqueous mist using an appropriate atomisation technique or apparatus, such as a nebulizer.

Anorectal administration is particularly useful when the condition to be treated is hemorrhoids or ulcerative colitis, using an appropriate delivery means, such as a solution of foam to be injected or a suppository.

Administration to the lower gastrointestinal tract may also be achieved by parenteral, and particularly by peroral, delivery, by means of standard delayed- or extended-release coating techniques known to those skilled in the art. In particular, distinct parts of the upper or lower intestine may be targeted. For example, colonic administration can also be achieved by way of colon-targeted drug delivery means that are initially administered perorally or parenterally.

Compounds of the invention may in the alternative be administered by direct systemic parenteral administration. Such administration may be useful in methods of treatment of an inflammatory and/or fibrotic disorder or condition of one or more internal organs of a patient.

Internal organs that may be mentioned include the stomach, the intestines, the pancreas, the liver, the spleen, the bladder, the vascular system, the ovaries, the prostate, preferably the heart and the kidneys and more preferably the lungs.

Fibrotic conditions of internal organs that may be mentioned include acute and/or severe internal fibrotic conditions characterised by the excessive accumulation of fibrous connective tissues (as described above) in and around inflamed or damaged tissues. Formulations of the invention may thus be useful in the treatment or prevention of fibrogenesis (as described above) and the morbidity and mortality that may be associated therewith. Thus, (e.g. acute and/or severe) fibrotic conditions of the internal organs that may be treated with formulations of the invention include fibrosis of the liver, the kidneys, the lungs, the cardiovascular system, including the heart and the vascular system, the pancreas, the spleen, the central nervous system (nerve fibrosis), bone marrow fibrosis, the eyes, the vagina, the cervix, etc.

Inflammatory conditions of internal organs include any condition that is, or may develop into a condition that is, severe (i.e. one that requires intensive medical treatment), and in which some sort of inflammatory component is apparent, as may be characterised by detectable inflammation, and further in which morbidity is manifested (or is expected) and/or is life-threatening.

Inflammatory conditions that may be mentioned include one or more acute disorders or conditions of internal organs (i.e. one or more conditions that require, or may develop into a condition that requires, immediate medical interventions) that are characterized by inflammation (e.g. as a symptom), such as acute internal injuries, in one or more internal organs (including any of the organs mentioned hereinbefore). By treating such acute inflammatory disorders, formulations of the invention may prevent or arrest the development of symptoms (acute or chronic) that are associated with such conditions, and also may arrest the progress of morbidity and/or mortality that is associated with such conditions.

Acute inflammatory conditions that may be mentioned thus include conditions such as peritonitis, pancreatitis, colitis, proctitis, gastritis, duodenitis, pharyngitis, GERD, parodontitis and stomatitis. Particular acute inflammatory conditions that may be mentioned include acute injury to one or more internal organs (including any of those mentioned hereinbefore), such as acute lung injury, inhalation injury (such as burns), acute respiratory distress syndrome (ARDS), severe acute respiratory syndrome (SARS), and multiple-organ inflammation, injury and/or failure.

Such conditions may be caused by internal or external trauma (e.g. injury or a burn), or by an infection by e.g. viruses, bacteria or fungi.

For example, proctitis (which includes eosinophilic, gonorrheal and/or ulcerative proctitis) may be caused by inflammatory bowel disease, infections, radiation (e.g. for cancer), drugs such as antibiotics, surgery or allergic conditions, such as food intolerances.

For example, multiple-organ inflammation, injury and/or failure may result from extensive and/or traumatic external injuries, including traumatic and/or extensive external burns. Traumatic external burns will be understood to include second-degree, and more particularly third-degree burns and fourth-degree, burns. Extensive external burns will be understood to include burns that affect at least about 10%, such as at least about 15%, including at least about 20% of a patient's body area. External (and internal) burns may result from exposure to heat, chemicals and the like.

Acute inflammatory and/or fibrotic conditions may also result from sepsis or septic shock, which can be caused by viral, bacterial or fungal infection. Furthermore, acute lung injury, ARDS and, particularly, SARS may be caused by viruses, such as coronaviruses, include the novel SARS coronavirus 2 (SARS-CoV-2).

Thus, in addition, one or more of the aforementioned (e.g. acute) inflammatory conditions may (indeed in some cases will likely) result in some form of internal tissue damage and/or dysfunction of relevant internal tissues. Relevant tissues thus include (e.g. mucosal) tissues, such as the respiratory epithelium. Such tissue damage may also give rise to one or more of the fibrotic conditions mentioned hereinbefore. For example, the SARS disease caused by the novel coronavirus SARS-CoV-2 (coronavirus disease 2019 or COVID-19) is known in many cases to result in fibrosis, which arise from one or more of a number of factors, including inflammation.

In this respect, compounds of the invention and salts thereof find particular utility in the treatment of relevant inflammatory and/or fibrotic conditions on the basis that such conditions are often characterized by one or more comorbidities. By conditions that are 'characterized by comorbidities', we include that the main condition in question results in (or from) one more further medical conditions, including (and indeed preferably) those mentioned hereinbefore, at the same time, which conditions may interact and/or overlap with each other in some way.

Thus, there are provided:

methods of treatment of at least one inflammatory and/or fibrotic disorder or condition of one or more internal organs of a patient, which method comprises direct systemic parenteral administration of a compound of the invention, or a pharmaceutically-acceptable salt thereof, to a patient in need of such treatment;

a method of treatment of two or more inflammatory and/or fibrotic disorders or conditions of one or more internal organs of a patient, which method comprises direct systemic parenteral administration of a compound of the invention, or a pharmaceutically-acceptable salt thereof, to a patient in need of such treatment; and a method of reduction in the incidence of morbidity and/or mortality that is or may be associated with one or more inflammatory and/or fibrotic disorders or conditions of one or more internal organs of a patient, which method comprises direct systemic parenteral administration of a compound of the invention, or a pharmaceutically-acceptable salt thereof, to a patient in need of such treatment.

When compounds of the invention/salts thereof are administered directly and parenterally, they may be administered intravenously, intraarterially, intravascularly, perivascularly, intramuscularly, cutaneously, and/or subcutaneously, for example by way of direct injection, or by way of any other parenteral route, in the form of a compound of the invention or salt thereof in the form of a pharmaceutically-acceptable dosage form.

Pharmaceutically-acceptable formulations for use in such administration may thus comprise compounds of the invention in admixture with a pharmaceutically-acceptable adjuvant, diluent or carrier, which may be selected with due regard to the intended route of direct parenteral administration and standard pharmaceutical practice. Such pharmaceutically-acceptable carriers may be chemically inert to the active compounds and may have no detrimental side effects or toxicity under the conditions of use. Such pharmaceutically-acceptable carriers may also impart an immediate, or a modified, release of the compound of the invention.

Formulations for injection may thus be in the form of an aqueous formulation such as an a suspension and/or, more preferably a solution (e.g. an (optionally) buffered aqueous formulation (e.g. solution), such as a physiological saline-containing formulation (e.g. solution), a phosphate-containing formulation (e.g. solution), an acetate-containing formulation (e.g. solution) or a borate-containing formulation (e.g. solution), or a freeze-dried powder that may be reconstituted with a vehicle, such as an aqueous vehicle prior to use (e.g. injection)).

Formulations for injection may include other suitable excipients known to those skilled in the art, such as solvents (e.g. water), co-solvents, solubilizing agents (e.g. cyclodextrins), wetting agents, suspending agents, emulsifying agents, thickening agents, chelating agents, antioxidants, reducing agents, antimicrobial preservatives, bulking agents and/or protectants.

Formulations for injection are preferably buffered by standard techniques to physiologically-acceptable pH values (e.g. pHs of between about 4.5 and about 9.5, e.g. about 6 and about 9, such as between about 6.5 and about 8.5) using buffers and/or pH modifiers as described herein, and/or may further comprise tonicity-modifying agents (such as sodium chloride).

The above notwithstanding, preferred modes of delivery of compounds of the invention include topically to the site of inflammation (e.g. the mucosa, including the oral and/or nasal mucosa, the lung, the anorectal area and/or the colon or, more preferably, the skin) in an appropriate (for example pharmaceutically- and topically-acceptable) vehicle suitable for application to the skin and/or the appropriate mucosal surface, and/or a commercially-available formulation, but may also include oral, intravenous, cutaneous or subcutaneous, nasal, intramuscular, intraperitoneal, or pulmonary delivery.

Administration by injection is particularly useful for administering the compound of the invention, in the form of a solution of suspension into e.g. the dermis (e.g. intradermal injection), joint cavity or the eyes.

Administration by intradermal injection (e.g. intradermally) is particularly useful for administering the compound of the invention, in the form of a solution or suspension (e.g. a dermal filler), into the dermis. This is particularly useful as a means of administration for melanin pigmentation therapy as described hereinbefore or for the use of the compounds of the invention in the treatment of, e.g. wrinkles.

Administration by injection is particularly useful to fill, e.g. the surgical site of the nasal cavity, the anal fistula, the space between the gingival and the root or the sinus.

Compounds of the invention will generally be administered in the form of one or more for example pharmaceutical formulations in admixture with a (e.g. pharmaceutically acceptable) adjuvant, diluent or carrier, which may be selected with due regard to the intended route of administration (e.g. topical to the relevant mucosa (including the lung) or, preferably, the skin) and standard pharmaceutical or other (e.g. cosmetic) practice. Such pharmaceutically acceptable carriers may be chemically inert to the active compounds and may have no detrimental side effects or toxicity under the conditions of use. Such pharmaceutically acceptable carriers may also impart an immediate, or a modified, release of the compound of the invention.

Suitable pharmaceutical formulations may be commercially available or otherwise prepared according to techniques that are described in the literature, for example, Remington *The Science and Practice of Pharmacy,* $22^{nd}$ edition, Pharmaceutical Press (2012) and *Martindale—The Complete Drug Reference,* $38^{th}$ Edition, Pharmaceutical Press (2014) and the documents referred to therein, the relevant disclosures in all of which documents are hereby incorporated by reference. Otherwise, the preparation of suitable formulations including compounds of the invention may be achieved non-inventively by the skilled person using routine techniques.

Compounds of the invention may be in the form of an aqueous formulation such as an emulsion, a suspension and/or a solution (e.g. an (optionally) buffered aqueous formulation (e.g. solution), such as a physiological saline-containing formulation (e.g. solution), a phosphate-containing formulation (e.g. solution), an acetate-containing formulation (e.g. solution) or a borate-containing formulation (e.g. solution)), or a freeze-dried powder.

Compounds of the invention may further and/or in the alternative be combined with appropriate excipients to prepare:

gel formulations (for which suitable gel matrix materials include cellulose derivatives, carbomer and alginates, gummi tragacanthae, gelatin, pectin, carrageenan, gellan gum, starch, Xanthan gum, cationic guar gum, agar, noncellulosic polysaccharides, saccharides such as glucose, glycerin, propanediol, vinyl polymers, acrylic resins, polyvinyl alcohol, carboxyvinyl polymer and, particularly, hyaluronic acid);

lotions (for which suitable matrix materials include cellulose derivatives, glycerin, noncellulosic polysaccharides, polyethylene glycols of different molecular weights and propanediol);

pastes or ointments (for which suitable paste matrix materials include glycerin, Vaseline, paraffin, polyethylene glycols of different molecular weights, etc.);

creams or foams (for which suitable excipients (e.g. foaming agents) include hydroxypropyl methyl cellulose, gelatin, polyethylene glycols of different molecular weights, sodium dodecyl sulfate, sodium fatty alcohol polyoxyethylene ether sulfonate, corn gluten powder and acrylamide);

powder aerosols (for which suitable excipients include mannitol, glycine, dextrin, dextrose, sucrose, lactose, sorbitol and polysorbates, e.g. a dry powder inhalant);

liquid, for example, water (aerosol) sprays for oral use or for inhalation (for which suitable excipients include viscosity modifiers, such as hyaluronic acid, sugars, such as glucose and lactose, emulsifiers, buffering agents, alcohols, water, preservatives, sweeteners, flavours, etc.); and/or injectable solutions or suspensions (which may be aqueous or otherwise and for which suitable excipients include solvents and co-solvents, solubilizing agents, wetting agents, suspending agents, emulsifying agents, thickening agents, chelating agents, antioxidants, reducing agents, antimicrobial preservatives, buffers and/or pH modifiers, bulking agents, protectants and tonicity-modifying agents), particular injectable solutions or suspensions that may be mentioned include dermal fillers (i.e. injectable fillers or soft-tissue fillers), particularly when the compound of the invention is combined with hyaluronic acid.

Moisturizing agents, such as glycerol, glycerin, polyethylene glycol, trehalose, glycerol, petrolatum, paraffin oil, silicone oil, hyaluronic acid and salts (e.g. sodium and potassium salts) thereof, octanoic/caprylic triglyceride, and the like; and/or antioxidants, such as vitamins and glutathione; and/or pH modifiers, such as acids, bases and pH buffers, may also be included in such formulations, as appropriate. Furthermore, surfactants/emulsifiers, such as hexadecanol (cetyl alcohol), fatty acids (e.g. stearic acid), sodium dodecyl sulfate (sodium lauryl sulfate), sorbitan esters (e.g. sorbitan stearate, sorbitan oleate, etc.), monoacyl glycerides (such as glyceryl monostearate), polyethoxylated alcohols, polyvinyl alcohols, polyol esters, polyoxyethylene alkyl ethers (e.g. polyoxyethylene sorbitan monooleate), polyoxyethylene castor oil derivatives, ethoxylated fatty acid esters, polyoxylglycerides, lauryl dimethyl amine oxide, bile salts (e.g. sodium deoxycholate, sodium cholate), lipids (e.g. fatty acids, glycerolipids, glycerophospholipids, sphingolipids, sterols, prenols, saccharolipids, polyketides), phospholipids, N,N-dimethyldodecylamine-N-oxide, hexadecyltrimethyl-ammonium bromide, poloxamers, lecithin, sterols (e.g. cholesterol), sugar esters, polysorbates, and the like; preservatives, such as phenoxyethanol, ethylhexyl glycerin, and the like; and thickeners, such as acryloyldimethyltaurate/VP copolymer, may be included. In particular, stearic acid, glyceryl monostearate, hexadecanol, sorbitan stearate, cetyl alcohol, octanoic/capric glyceride etc. may be included, particularly in cream formulations.

Compounds of the invention, and (e.g. pharmaceutical) formulations (e.g. aqueous solutions, gels, creams, ointments, lotions, foams, pastes and/or dry powders as described above) including them, may further be combined with an appropriate matrix material to prepare a dressing or a therapeutic patch for application on a biological surface, such as the skin or a mucosal surface. Such formulations may thus be employed to impregnate a matrix material, such as gauze, non-woven cloth or silk paper. The therapeutic patch may alternatively be, for example, a band-aid, a facial mask, an eye mask, a hand mask, a foot mask, etc.

Vaseline may be employed for use in applying such dressings to wounds, but we have also found that ointments based on PEGs (e.g. PEG 400) may be combined with matrix materials to prepare dressings without the need to use Vaseline.

Compounds of the invention may also be used in combination with solid supports (such as nasal dressings (for example, to stop nasal bleeding), dermal scaffolds (for example, in wound healing) or artificial bones (for example, in the case of bone grafting/implantation).

Compounds of the invention may be administered for inhalation by way of suspension, a dry powder or a solution. Suitable inhalation devices include pressurized metered-dose inhalers (pMDIs), which may be hand- or breath-actuated and employed with or without a standard spacer device, dry powder inhalers (DPIs), which may be single-dose, multi-dose, and power-assisted, and soft mist inhalers (SMIs) or nebulizers, in which aerosol drug in a fine mist is delivered with slower velocity than a spray delivered using, for example, a pMDI.

In pMDIs, compounds of the invention may be administered as a pressurized suspension of micronized particles distributed in a propellant (e.g. HFA, along with excipients, such as mannitol, lactose, sorbitol, etc.), or as an ethanolic solutions, to deliver one or more metered dose of between about 20 and about 100 μL with each actuation. Actuation may be effected by hand (e.g. pressing) or by inhalation (breath-actuation), involving a flow-triggered system driven by a spring.

In DPIs, compounds of the invention may be administered in the form of micronized drug particles (of a size between about 1 and about 5 μm), either alone or blended with inactive excipient of larger particle size (e.g. mannitol), inside a capsule, which may be pre-loaded or manually loaded into the device. Inhalation from a DPI may de-aggregate the medication particles and disperse them within the airways.

In SMIs, compounds of the invention may be stored as a solution inside a cartridge, which is loaded into the device. A spring may release the dose into a micropump, such that the dose is released when a button is pressed, releasing jet streams of drug solution.

Various nebulizers may also be used to administer compounds of the invention in the form of a fine mist of aerosolized solution. Nebulizers may include breath-enhanced jet nebulizer (in which, with the assistance of a compressor, an air stream moves through jet causing drug solution to be aerosolized); breath-actuated jet nebulizers (in which, after a patient inhales, with the assistance of a compressor, an air stream moves through a tube causing the drug solution to be aerosolized); ultrasonic nebulizers (in which piezoelectric crystals vibrate causing aerosolization by heating causing nebulization); vibrating mesh nebulizers (in which piezoelectric crystals vibrate a mesh plate causing aerosolization to give very fine droplets without a significant change in temperature of the solution during nebulization).

According to a further aspect of the invention there is provided a process for the preparation of a pharmaceutical composition/formulation, as defined herein, which process comprises bringing into association a compound of the invention, as hereinbefore defined, with one or more pharmaceutically-acceptable excipient, as hereinbefore defined.

Compounds of the invention may also be combined in treatment with one or more growth factors selected from platelet-type growth factors (including platelet-derived growth factors, PDGFs); osteosarcoma-derived growth factors (ODGF), epidermal growth factors (EGFs), transforming growth factors (TGFα and TGFβ), fibroblast growth factors (αFGF, βFGF), insulin-like growth factors (IGF-I, IGF-II), nerve growth factors (NGF), interleukin-type growth factors (IL-1, IL-1, IL-3), erythropoietin (EPO), and colony stimulating factor (CSF).

According to a further aspect of the invention there is provided a (e.g. pharmaceutical) composition comprising a compound of the invention and one or more pharmaceutically-acceptable excipient, such as an adjuvant, diluent or carrier. Preferred formulations are suitable for application locally to e.g. the mucosa (including the oral and/or nasal mucosa, the lung, the anorectal area and/or the colon) or, more preferably, the skin and therefore comprise a topically-acceptable adjuvant, diluent or carrier.

There is, thus, further provided pharmaceutical compositions comprising compounds of the invention that are suitable for, adapted for, and/or packaged and presented for topical administration (e.g. to the mucosa, including the oral and/or nasal mucosa, the lung, the anorectal area and/or the colon, or, preferably, to the skin), as well as the use of such a formulation in the treatment of a disorder including inflammation, an inflammatory disorder and/or a condition characterized by inflammation (e.g. as a symptom) by way of direct topical administration of that formulation (e.g. to the mucosa, including the oral and/or nasal mucosa, the lung, the anorectal area and/or the colon, or, preferably, to the skin).

In relation to this aspect of the invention, for the avoidance of doubt, topical formulations comprising compounds of the invention may be used in any and all conditions described herein, including treatments of inflammation, in the treatment of any and all inflammatory disorder(s), and/or in the treatment of any and all condition(s) characterized by inflammation, as hereinbefore mentioned, defined or described. Similarly, topical formulations comprising compounds of the invention that may be mentioned include any and all of those mentioned, defined or described herein. Any and all of the relevant disclosures herein are hereby incorporated by reference in conjunction with this aspect of the invention.

Topical (e.g. liquid- or (e.g. aqueous) solution-based) formulations comprising compounds of the invention may be particularly useful in wound recovery, and may alleviate pain (including aching) and, particularly, pruritis/itching that is associated with the wound itself and the wound healing process. Such topical formulations comprising compounds of the invention may be particularly useful in the prevention and/or suppression of the exudation of body fluids from wounds, particularly during the acute inflammation stage, for example during the first 48 hours, after a burn or wound has been inflicted. This prevents the risk of infection, and other physiological reactions. Such topical formulations comprising compounds of the invention may also be particularly useful in the prevention and/or suppression of scarring and melanin pigmentation (vide supra), whether associated with wounds or otherwise.

Administration of compounds of the invention may be continuous or intermittent. The mode of administration may also be determined by the timing and frequency of administration, but is also dependent, in the case of the therapeutic treatment of inflammation, on the severity of the condition.

Depending on the disorder, and the patient, to be treated, as well as the route of administration, compounds of the invention may be administered at varying therapeutically effective doses to a patient in need thereof.

Similarly, the amount of compound of the invention in a formulation will depend on the severity of the condition, and on the patient, to be treated, but may be determined by the skilled person.

In any event, the medical practitioner, or other skilled person, will be able to determine routinely the actual dosage, which will be most suitable for an individual patient, depending on the severity of the condition and route of administration. The dosages mentioned herein are exemplary of the average case; there can, of course, be individual instances where higher or lower dosage ranges are merited, and such are within the scope of this invention.

Doses may be administered between once and four (e.g. three) times daily.

Appropriate concentrations of compounds of the invention in an aqueous solution product may be about 0.01 (e.g. about 0.1) to about 15.0 mg/mL, in all cases calculated as the free (non-salt) compound.

Appropriate topical doses of compounds of the invention are in the range of about 0.05 to about 50 $\mu g/cm^2$ of treated area, such as about 0.1 (e.g. about 0.5) to about 20 $\mu g/cm^2$ of treated area, including about 1 to about 10 $\mu g/cm^2$ of treated area, such as about 5 $\mu g/cm^2$ of treated area, in all cases calculated as the free (non-salt) compound.

Appropriate doses of compounds of the invention for nasal administration (e.g. by inhalation) are in the range of about 0.01 μg to about 2000 mg, for example between about 0.1 μg to about 500 mg, or between 1 μg to about 100 mg. Particular doses for nasal administration that may be mentioned include between about 10 μg to about 1 mg, particularly a dose of about 0.1 mg (i.e. about 100 μg). Nasal administration of about 0.1 mg per day of compounds of the invention has been found to be particularly effective in the treatment of conditions associated with inflammation of the nasal passages and mucosae, such as rhinitis (e.g. allergic rhinitis) and/or conditions associated with nasosinusitis surgery.

Appropriate doses of compounds of the invention for pulmonary administration (e.g. by inhalation) are in the range of about 0.01 μg to about 2000 mg, for example between about 0.1 μg to about 500 mg, or between 1 μg to about 100 mg. Particular doses for pulmonary administration that may be mentioned include between about 10 μg to about 10 mg, particularly a dose of about 0.6 mg (i.e. 60 μg) to 6 mg (e.g. for use in treating COPD or IPF).

We prefer that pH values of formulations comprising compounds of the invention are in the range of about 1.0 to about 9.0 (for example about 3.0 to about 8.0).

In any event, the dose administered to a mammal, particularly a human, in the context of the present invention should be sufficient to effect a therapeutic response in the mammal over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

Compounds of the invention may be used as human, and/or animal, medicines.

In the uses and methods described herein, compounds of the invention may also be combined with one or more pharmaceutically-active ingredients that are useful in the treatment of inflammation and/or inflammatory disorders (other antiinflammatory agents).

Such patients may thus also (and/or may already) be receiving therapy based upon administration of one or more of such other, known pharmaceutically-active ingredients, by which we mean receiving a prescribed dose of one or more of the active ingredients mentioned herein, prior to, in addition to, and/or following, treatment with a compound of the invention.

Non-limiting examples of other anti-inflammatory agents which may be used also include those used in the treatment of rheumatic diseases and/or arthritis (such as cataflam, betamethasone, naproxen, cyclosporin, chondroitin, celecoxib, etodolac, meclofenamate, salsalate, methylprednisolone, and piroxicam); osteoarthritis (such as sulindac, meloxicam, fenoprofen, etoricoxib, and nabumetone); inflammation and its symptoms, e.g. fever, pain, itchiness and/or swelling (such as mefenamic acid, indomethacin, aspirin, ketorolac, fluorometholone, loteprednol, hydrocortisone, fluorometholone, bromfenac, prednisolone acetate, indomethacin, and ibuprofen); allergies and their symptoms (such as pheniramine, diphenhydramine, naphazoline, antazoline, prednisolone, lodoxamide, pemirolast, oxymetazoline, ketotifen, naphazoline, emestine fumarate, olopatadine, azelastine, tranilast, levocabastine, cortisone, ephedrine, cetirizine, levocetirizine, pseudophedrine, fexofenadine, terfenadine, loratadine, and alexis); respiratory diseases, including asthma and/or COPD (such as budesonide, ciclesonide, nedocromil, dexamethasone, ambroxol, and pranlukast); skin diseases (such as mometasone, triamcinolone, desonide, sulfacetamide, tacrolimus, allantoin, and triamcinolone); mastocytosis (such as cromolyn); gout (such as diclofenac, and febuxostat); conjunctivitis (such as hydrobenzole, pranoprofen, and zinc sulfate); eye diseases (such as dextran 70, thyroxine/liothyronine, and ocular extractives), known or commercially-available pharmaceutically acceptable salts of any of the foregoing, and combinations of any of the forgoing compounds and/or salts.

Antiinflammatory drugs that may be mentioned include endogenous (and/or exogenous) lipid-based pro-resolving, antiinflammatory molecules or mediators, such as lipoxins, resolvins, and protectins. Pro-inflammatory agents that may be mentioned include prostaglandins (e.g. latanoprost, prostaglandin E1, and prostaglandin E2), and leukotrienes (e.g. Leukotriene B4).

Other anti-inflammatory agents that may in particular be used in combination with compounds of the invention in the treatment of inflammation include therapeutic agents that are useful in the treatment of inflammation and/or of diseases characterized by inflammation as one of its symptoms, including those described hereinbefore. Depending on the condition to be treated, such anti-inflammatory agents may include NSAIDs (e.g. aspirin), aminosalysates (e.g. 5-aminosalicyclic acid (mesalazine)), leukotriene receptor antagonists (e.g. montelukast, pranlukast, and zafirlukast), corticosteroids, analgesics and certain enzymes, such as trypsin, for example as described hereinafter. Compounds of the invention may also be combined with leukotrienes (e.g. cysteinyl leukotrienes, and leukotriene B4).

Other preferred agents that may be combined with compounds of the invention include LTB4 (to treat wounds and burns), NSAIDS (e.g. aspirin) or montelukast (to treat inflammation generally) and trypsin (to treat inflammation of the mucosa associated with e.g. viral infections).

Compounds of the invention may also be combined with other therapeutic agents which, when administered, are known to give rise to inflammation as a side-effect.

Compounds of the invention may also be combined with stem cells (e.g. totipotent (omnipotent), pluripotent (such as embryonic or induced pluripotent stem cells), multipotent (such as mesenchymal stem cells), oligopotent (such as hematopoietic stem cells), or unipotent (such as muscle stem cells)).

Other known pharmaceutically-active (e.g. antiinflammatory) ingredients may also be administered in combination with compounds of the invention in numerous ways.

For example, compounds of the invention may be 'combined' with the other pharmaceutically-active ingredients (or 'therapeutic agents') for administration together in the same (e.g. pharmaceutical) formulation, or administration separately (simultaneously or sequentially) in different (e.g. pharmaceutical) formulations.

Thus, such combination products provide for the administration of compounds of the invention in conjunction with the other therapeutic agent, and may thus be presented either as separate formulations, wherein at least one of those formulations comprises a compound of the invention, and at least one comprises the (or the other) therapeutic agent, or may be presented (i.e. formulated) as a combined preparation (i.e. presented as a single formulation including a compound of the invention and the (or the other) therapeutic agent).

Thus, there is further provided:

(1) a (e.g. pharmaceutical) formulation including a compound of the invention; another antiinflammatory agent, or agent known to give rise to inflammation as a side effect; and a pharmaceutically-acceptable excipient (e.g. adjuvant, diluent or carrier), which formulation is hereinafter referred to as a 'combined preparation'; and (2) a kit of parts comprising components:

(A) a pharmaceutical formulation including a compound of the invention in admixture with a pharmaceutically-acceptable inactive excipient (e.g. adjuvant, diluent or carrier); and (B) a pharmaceutical formulation including another anti-inflammatory agent, or agent known to give rise to inflammation as a side effect in admixture with a pharmaceutically-acceptable adjuvant, diluent or carrier, which components (A) and (B) are each provided in a form that is suitable for administration in conjunction with the other.

In a further aspect of the invention, there is provided a process for the preparation of a combined preparation (1) as hereinbefore defined, which process comprises bringing into association a compound of the invention, the other antiinflammatory agent, or agent known to give rise to inflammation as a side effect, and at least one (e.g. pharmaceutically-acceptable) excipient.

In a further aspect of the invention, there is provided a process for the preparation of a kit-of-parts (2) as hereinbefore defined, which process comprises bringing into association components (A) and (B). As used herein, references to bringing into association will mean that the two components are rendered suitable for administration in conjunction with each other.

Thus, in relation to the process for the preparation of a kit-of-parts as hereinbefore defined, by bringing the two components 'into association with' each other, we include that the two components of the kit-of-parts may be:

(i) provided as separate formulations (i.e. independently of one another), which are subsequently brought together for use in conjunction with each other in combination therapy; or (ii) packaged and presented together as separate components of a 'combination pack' for use in conjunction with each other in combination therapy.

Thus, there is further provided a kit of parts comprising:

(I) one of components (A) and (B) as defined herein; together with (II) instructions to use that component in conjunction with the other of the two components.

The kits of parts described herein may comprise more than one formulation including an appropriate quantity/dose of a compound of the invention, and/or more than one formulation including an appropriate quantity/dose of the other antiinflammatory agent, in order to provide for repeat dosing. If more than one formulation comprising or quantity/dose of either active compound is present, such may be the same, or may be different in terms of the dose of either compound, chemical composition(s) and/or physical form(s).

With respect to the kits of parts as described herein, by 'administration in conjunction with', we include that respective formulations comprising a compound of the invention and other antiinflammatory are administered, sequentially, separately and/or simultaneously, over the course of treatment of the relevant condition.

Thus, in respect of the combination product according to the invention, the term 'administration in conjunction with' includes that the two components of the combination product (compound of the invention and other antiinflammatory agent) are administered (optionally repeatedly), either together, or sufficiently closely in time, to enable a beneficial effect for the patient, that is greater, over the course of the treatment of the relevant condition, than if either a formulation comprising compound of the invention, or a formulation comprising the other agent, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit of parts according to the invention, the term 'in conjunction with' includes that one or other of the two components may be administered (optionally repeatedly) prior to, after, and/or at the same time as, administration of the other component. When used in this context, the terms 'administered simultaneously' and 'administered at the same time as' include that individual quantities/doses of the relevant compound of the invention and other antiinflammatory agent are administered within 48 hours (e.g. 24 hours) of each other.

Wherever the word 'about' is employed herein, for example in the context of amounts, such as concentrations and/or doses of compounds of the invention and/or active ingredients, molecular weights or pHs, it will be appreciated that such variables are approximate and as such may vary by ±10%, for example ±5% and preferably ±2% (e.g. ±1%) from the numbers specified herein. In this respect, the term 'about 10%' means e.g. ±10% about the number 10, i.e. between 9% and 11%.

Compounds of the invention have the advantage that they may be used in variety of conditions characterised by inflammation, whether that condition is an organic inflammatory disease perse or is associated with, or is characterised by, inflammation (e.g. a wound or a burn), and/or in surgical and/or cosmetic applications as described hereinbefore.

The compounds, uses and methods described herein may also have the advantage that, in the treatment of the conditions mentioned hereinbefore, they may be more convenient for the physician and/or patient than, be more efficacious than, be less toxic than, have a broader range of activity than, be more potent than, produce fewer side effects than, or that it/they may have other useful pharmacological properties over, similar compounds or methods (treatments) known in the prior art, whether for use in the treatment of inflammation, inflammatory disorders, or disorders characterised by inflammation as a symptom (including wounds), or otherwise.

The invention is illustrated, but in no way limited, by the following examples, in which FIG. 1 shows Evans blue content in rectal and anal tissue indicating vascular permeability of test compounds.

EXAMPLES

Example 1

DOPA-Ala-Lys-Pro-Ser-Tyr-Hyp-Thr-Tyr-Hyp-Lys (SEQ ID No: 7)

Fmoc-Lys(Boc)-Wang resin (9.15 g, 41301, GL Biochem, Shanghai, China) was loaded into a glass reaction column.

Methylene chloride (DCM, 200 mL; Shandong Jinling Chemical Industry Co. Ltd., Shandong, China) was added to the column and allowed to soak the resin for about half an hour. The DCM was then removed by vacuum filtration.

The resin was washed 3 times with N,N-dimethylformamide (DMF, 200 mL; Shandong Shitaifeng Fertilizer Industry Co Ltd, Shandong, China).

A 20% piperidine solution in DMF (200 mL; Shandong Shitaifeng Fertilizer Industry Co Ltd, Shandong, China) was added as deprotection solution and reacted for 20 minutes. The solution was then removed by vacuum filtration and the resin in the column was washed with DMF six times.

Fmoc-4-Hyp(tBu)-OH (3.68 g; 21303, GL Biochem, Shanghai, China) and 2-(1H-benzotriazole-1-yl)-1,1,3,3-tetramethylaminium tetrafluoroborate (TBTU, 2.89 g; 00705, GL Biochem, Shanghai, China) were added to the resin. DMF (150 mL) was added to the reaction column, followed by N,N-diisopropylethylamine (DIPEA, 2.33 g; Suzhou Highfine Biotech Co. Ltd, Jiangsu, China). A Kaiser Test was carried out with few of the resin after 30 minutes reaction, a yellow color of the solution and colorless gel indicating the reaction was complete. The solvent was removed by vacuum filtration.

The above coupling steps were repeated to couple the remaining amino acids in the same amounts (by mols): Fmoc-Tyr(tBu)-OH, Fmoc-Thr(tBu)-OH, Fmoc-4-Hyp (tBu)-OH, Fmoc-Tyr(tBu)-OH, Fmoc-Ser(tBu)-OH, Fmoc-Pro-OH, Fmoc-Lys(Boc)-OH, Fmoc-Ala-OH and Fmoc-DOPA(Acetonide)-OH.

In a separate procedure, after Fmoc-DOPA(Acetonide)-OH was coupled on the resin, a deprotection step was carried out to remove the Fmoc protection on Dopa. The resin was washed 3 times with DMF (200 mL each time). A 20% piperidine solution in DMF (200 mL) was added as a deprotection solution and reacted for 20 minutes. Then, the resin was washed three times each with the following solvents, DMF (200 mL each time), DCM (200 mL each time) and methanol (200 mL each time; Xilong Scientific Co., Ltd., Guangdong, China). The resin was dried under vacuum for about 2 hours.

130.0 mL (i.e. 10 mL per gram of the dried resin) of lysate, which comprised of 95% trifluoroacetic acid (TFA), 2.5% water and 2.5% triisopropylsilane (Tis), were added to immerse the resin-bounded peptide-containing compound. After cleavage for about 2 hours, the solid support was removed by filtration and the filtrate was collected under reduced pressure. The filtrate was precipitated with 1300 mL (i.e. 10 mL per ml of the filtrate) of diethyl ether (Xilong Scientific Co., Ltd., Guangdong, China) and the sediment was collected by filtration. The sediment was dried by vacuum for about 2 hours, yielding 4.53 g of crude title compound.

The crude product was firstly analyzed as a 1 mg/mL sample in pure water and detected using a Shimadzu LCMS-8050 system. The analysis column was an Agilent ZORBAX Eclipse SB-C18 (4.6×250 mm, 5 μm column; detection: UV at 220 nm; solvent A: 0.1% TFA in MeCN, solvent B: 0.1% TFA in water, with a linear gradient from 5%~90% solvent A concentration in 50 minutes; flow rate 1.0 mL/min; sample volume: 10 μL).

The target peak was eluted at 9.719 minutes and had the expected molecular weight, with a purity of 79.363%.

MS: m/z 1362.4

4.5 g of crude product was then dissolved in 50 mL of pure water and purified using LC3000 semi-preparation equipment. The preparation column model was a Dubhe-C18 model (Hanbon Sci. &Tech. Co., Ltd., Jiangsu, China) (50*250 mm, 100 Å column; detection: UV at 220 nm). The appropriate gradient for elution was calculated from LCMS detection step (Solvent A: 0.1% TFA in MeCN, solvent B: 0.1% TFA in water, with a linear gradient from 5%~20% solvent A concentration in 30 minutes; flow rate 60.0 mL/min). Fractions were collected and analyzed using a Shimadzu LC-20 HPLC system (column as above, except with a linear gradient from 5%-30% solvent A concentration in 25 minutes).

Fractions with a purity of 98% were then mixed together for an anion exchange step. This was achieved using a LC3000 semi-preparation equipment (preparation column model: Dubhe-C18 model (as above). The fractions were diluted one time with pure water and loaded to the column directly, after that the column was washed with 0.37% of ammonium acetate in pure water for about 20 minutes followed by pure water for another 20 minutes at the flow rate of 60 mL/min, then eluted with the following gradient (Solvent A: 0.1% HAc in MeCN, solvent B: 0.1% HAc in water, with a linear gradient from 5%~20% solvent A concentration in 30 minutes; flow rate 60.0 mL/min). Fractions were collected and analyzed using Shimadzu LC-20 HPLC system (column and conditions as above). Fractions with a purity of 98% were mixed and freeze-dried to give 3.23 g of the purified title compound.

Example 2

Synthesis of Further Peptides I

The following peptides were synthesised using essentially the same procedure as that described in Example 1 above, except that appropriate amino acids were used as appropriate in the relevant peptide coupling sequences:

```
                                   (SEQ ID No: 33)
Ala-Lys-Pro-Ser-Tyr-Hyp-Thr-Tyr-Hyp-Lys;

                                   (SEQ ID No: 34)
Ala-Lys-Pro-Ser-Tyr-Hyp-Thr-DOPA-Hyp-Lys;

                                   (SEQ ID No: 36)
Ala-Lys-Pro-Ser-DOPA-Hyp-Thr-DOPA-Hyp-Lys;

                                    (SEQ ID No: 6)
DOPA-Lys-Pro-Ser-Tyr-Hyp-Hyp-Thr-Ala-Lys;

                                   (SEQ ID No: 29)
DOPA-Lys-Pro-Ser-DOPA-Hyp-Hyp-Thr-Ala-Lys;

                                    (SEQ ID No: 5)
DOPA-Lys-Pro-Ser-Tyr-Hyp-Thr-Ala-Hyp-Lys;

                                   (SEQ ID No: 28)
DOPA-Lys-Pro-Ser-DOPA-Hyp-Thr-Ala-Hyp-Lys;

                                    (SEQ ID No: 9)
DOPA-Ala-Lys-Pro-Ser-Tyr-Hyp-Thr-DOPA-Hyp-Lys;

                                   (SEQ ID No: 30)
DOPA-Ala-Lys-Pro-Ser-DOPA-Hyp-Thr-DOPA-Hyp-Lys;
```

-continued (SEQ ID No: 8)
DOPA-Ala-Lys-Pro-Ser-Tyr-Hyp-Hyp-Thr-Tyr-Lys;

(SEQ ID No: 10)
DOPA-Ala-Lys-Pro-Ser-Tyr-Hyp-Hyp-Thr-DOPA-Lys;
and (SEQ ID NO: 32)
DOPA-Ala-Lys-Pro-Ser-DOPA-Hyp-Hyp-Thr-DOPA-Lys.

The crude yields and purity, retention time, MS values and final yields from these peptide syntheses were as shown in Table 1 below.

TABLE 1

| SEQ ID No. | Crude amount | Crude purity | Retention time | MS | Final amount |
|---|---|---|---|---|---|
| 33 | 4.59 g | 77.392% | 9.395 | 1183.3 | 2.87 g |
| 34 | 4.38 g | 79.176% | 9.957 | 1199.5 | 2.94 g |
| 36 | 4.94 g | 75.843% | 9.764 | 1215.2 | 2.97 g |
| 6 | 4.63 g | 76.125% | 9.356 | 1199.3 | 2.89 g |
| 29 | 4.75 g | 74.934% | 9.798 | 1215.1 | 2.96 g |
| 5 | 4.86 g | 78.312% | 9.456 | 1199.4 | 2.85 g |
| 28 | 4.95 g | 77.121% | 9.334 | 1215.5 | 2.99 g |
| 9 | 5.14 g | 79.853% | 9.562 | 1378.3 | 3.13 g |
| 30 | 5.23 g | 75.123% | 9.556 | 1395.6 | 3.22 g |
| 8 | 5.15 g | 77.944% | 9.662 | 1362.5 | 3.08 g |
| 10 | 5.17 g | 77.865% | 9.635 | 1378.4 | 3.11 g |
| 32 | 5.29 g | 76.947% | 9.593 | 1395.6 | 3.26 g |

Example 3

Lys-Ala-Lys-Pro-Ser-Tyr-Hyp-Hyp-Thr-DOPA (SEQ ID No: 54)

The title compound was prepared using essentially the same process as described in Example 1 above, except that Fmoc-Dopa(acetonide)-Wang resin (9.72 g, USUN Pharma. Jiangyin, China) was used instead of Fmoc-Lys(Boc)-Wang resin in the very beginning of peptide synthesis. This peptide is synthesized from Dopa as the first amino acid, then Fmoc-Thr(tBu)-OH, Fmoc-4-Hyp(tBu)-OH, Fmoc-4-Hyp (tBu)-OH, Fmoc-Tyr(tBu)-OH, Fmoc-Ser(tBu)-OH, Fmoc-Pro-OH, Fmoc-Lys(Boc)-OH, Fmoc-Ala-OH and Fmoc-Lys (Boc)-OH was coupled in the same process as described in Example 1 above.

MS: m/z 1199.3

Repeating essentially the same procedure gave a further batch of crude title compound (yield 5.22 g). Analysis showed a target peak that was eluted at 10.012 minutes with the expected molecular weight (MS: m/z 1199.3). The purity was 79.832%.

5.2 g of the crude product was then purified as described in Example 1 above to give 3.3 g of pure title compound after freeze-drying.

Example 4

Synthesis of Further Peptides II

The following peptides were synthesised using essentially the same procedure as that described in Example 3 above, except that appropriate amino acids were used as appropriate in the relevant peptide coupling sequences:

(SEQ ID No: 57)
Lys-Ala-Lys-Pro-Ser-DOPA-Hyp-Hyp-Thr-DOPA;

-continued (SEQ ID No: 56)
Lys-Ala-Lys-Hyp-Ser-Tyr-Hyp-Hyp-Thr-DOPA;

(SEQ ID No: 59)
Lys-Ala-Lys-Hyp-Ser-DOPA-Hyp-Hyp-Thr-DOPA;

(SEQ ID No: 38)
Ala-Lys-Pro-Ser-Tyr-Hyp-Thr-Tyr-Hyp-Lys-DOPA;

(SEQ ID No: 48)
Ala-Lys-Pro-Ser-Tyr-Hyp-Thr-DOPA-Hyp-Lys-DOPA;

(SEQ ID No: 50)
Ala-Lys-Pro-Ser-DOPA-Hyp-Thr-DOPA-Hyp-Lys-DOPA;

(SEQ ID No: 41)
Ala-Lys-Pro-Ser-Tyr-Hyp-Hyp-Thr-Tyr-Lys-DOPA;

(SEQ ID No: 42)
Ala-Lys-Pro-Ser-Tyr-Hyp-Hyp-Thr-DOPA-Lys-DOPA;
and (SEQ ID NO: 44)
Ala-Lys-Pro-Ser-DOPA-Hyp-Hyp-Thr-DOPA-Lys-DOPA.

The crude yields and purity, retention time, MS values and final yields from these peptide syntheses were as shown in Table 2 below.

TABLE 2

| SEQ ID No. | Crude amount | Crude purity | Retention time | MS | Final amount |
|---|---|---|---|---|---|
| 57 | 5.19 g | 77.392% | 10.195 | 1215.3 | 3.26 g |
| 56 | 5.08 g | 79.176% | 10.057 | 1215.5 | 3.34 g |
| 59 | 4.94 g | 75.843% | 10.164 | 1231.3 | 3.17 g |
| 38 | 5.23 g | 76.125% | 10.156 | 1362.5 | 3.19 g |
| 48 | 5.05 g | 74.934% | 10.198 | 1378.3 | 3.26 g |
| 50 | 5.22 g | 78.867% | 10.037 | 1394.2 | 3.38 g |
| 41 | 5.12 g | 79.393% | 10.129 | 1362.3 | 3.33 g |
| 42 | 4.04 g | 78.938% | 10.321 | 1378.2 | 3.39 g |
| 44 | 5.13 g | 77.876% | 10.235 | 1394.4 | 3.41 g |

Example 5

(SEQ ID NO: 17)
HCA-Ala-Lys-Pro-Ser-Tyr-Hyp-Thr-Tyr-Hyp-Lys

The title compound was prepared using essentially the same process as that described in Example 1 above, except that the last amino acid used here was 3,4-dihydroxyhydrocinnamic acid (1.64 g, Macklin, Shanghai, China) instead of Fmoc-DOPA(Acetonide)-OH used in example 1. After 3,4-dihydroxyhydrocinnamic acid was coupled on the resin, the resin could be directly washed with DMF, DCM and methanol without the deprotection step in example 1. Other procedures were exactly the same as example 1 to yield 4.89 g of crude title compound.

MS: m/z 1347.8

Analysis showed a target peak that was eluted at 9.667 minutes with the expected molecular weight (MS: m/z 1347.8). The purity was 77.957%.

4.8 g of the crude product was then purified as described in Example 1 above to give 3.4 g of pure title compound after freeze-drying.

Example 6

Synthesis of Further Peptides III

The following peptides were synthesised using essentially the same procedure as that described in Example 5 above, except that appropriate amino acids were used as appropriate in the relevant peptide coupling sequences:

```
(SEQ ID No: 15)
HCA-Lys-Pro-Ser-Tyr-Hyp-Hyp-Thr-Ala-Lys;

(SEQ ID No: 18)
HCA-Ala-Lys-Pro-Ser-Tyr-Hyp-Thr-DOPA-Hyp-Lys;

(SEQ ID No: 19)
HCA-Ala-Lys-Pro-Ser-DOPA-Hyp-Thr-DOPA-Hyp-Lys;

(SEQ ID No: 20)
HCA-Ala-Lys-Pro-Ser-Tyr-Hyp-Hyp-Thr-Tyr-Lys;

(SEQ ID No: 21)
HCA-Ala-Lys-Pro-Ser-Tyr-Hyp-Hyp-Thr-DOPA-Lys;

(SEQ ID No: 22)
HCA-Ala-Lys-Pro-Ser-DOPA-Hyp-Hyp-Thr-DOPA-Lys;

(SEQ ID No: 25)
HCA-Lys-Pro-Ser-Tyr-Hyp-Thr-Ala-Hyp-Lys;

(SEQ ID No: 26)
HCA-Lys-Pro-Ser-DOPA-Hyp-Thr-Ala-Hyp-Lys;
and

(SEQ ID NO: 27)
HCA-Lys-Pro-Ser-DOPA-Hyp-Hyp-Thr-Ala-Lys.
```

The crude yields and purity, retention time, MS values and final yields from these peptide syntheses were as shown in Table 3 below.

TABLE 3

| SEQ ID No. | Crude amount | Crude purity | Retention time | MS | Final amount |
|---|---|---|---|---|---|
| 15 | 4.59 g | 77.392% | 9.395 | 1184.3 | 3.47 g |
| 18 | 4.38 g | 79.176% | 9.957 | 1363.6 | 3.34 g |
| 19 | 4.94 g | 75.843% | 9.764 | 1379.7 | 3.57 g |
| 20 | 4.63 g | 76.125% | 9.356 | 1347.3 | 3.39 g |
| 21 | 4.85 g | 74.934% | 9.798 | 1363.5 | 3.46 g |
| 22 | 4.72 g | 76.237% | 9.798 | 1379.8 | 3.48 g |
| 25 | 4.69 g | 78.958% | 9.798 | 1184.4 | 3.23 g |
| 26 | 4.93 g | 75.303% | 9.798 | 1200.3 | 3.67 g |
| 27 | 4.88 g | 79.058% | 9.798 | 1200.2 | 3.63 g |

Example 7

Ala-Lys-Pro-Ser-Tyr-Hyp-Thr-Tyr-Hyp-Lys-Dopamine (SEQ ID No: 39)

The title compound was synthesized from Lys as the first amino acid with Fmoc-Lys(Boc)-Wang resin, using almost the same process as described in Example 1 above, Fmoc-4-Hyp(tBu)-OH, Fmoc-Tyr(tBu)-OH, Fmoc-Thr(tBu)-OH, Fmoc-4-Hyp(tBu)-OH, Fmoc-Tyr(tBu)-OH, Fmoc-Ser (tBu)-OH, Fmoc-Pro-OH, Fmoc-Lys(Boc)-OH and Boc-Ala-OH was coupled in the same process as described in Example 1 above.

After Boc-Ala-OH was coupled on the resin, the resin was washed three times each with the following solvents, DMF (200 mL each time), DCM (200 mL each time) and methanol (200 mL each time). Then the resin is dried by vacuum for about 2 hours.

120.0 mL (i.e. 10 mL per gram of the dried resin) of lysate, which comprised of 2% trifluoroacetic acid (TFA) in DCM, was added to immerse the resin-bounded peptide-containing compound. After cleavage for about 2 hours, the solid support was removed by filtration and the filtrate is collected under reduced pressure. Then the filtrate was concentrated by rotary distillation under reduced pressure. After all solvents were removed, DMF (100 mL) was added to the flask to dissolve the solid, Dopamine hydrochloride (1.71 g, Aladdin, Shanghai, China), TBTU (2.89 g), and DIPEA (2.33 g) were added to the reaction solution. After 30 minutes of the reaction, the reaction was completed. Precipitation of the final solution was carried out by adding 1200 mL (i.e. 10 mL per ml of the final solution) of saturated citric acid (Aladdin, Shanghai, China) water solution and sediment is collected by filtration. The sediments was then added 120 mL (i.e. 10 mL per gram of the solid) of lysate, which comprised of 95% trifluoroacetic acid (TFA), 2.5% water and 2.5% triisopropylsilane (Tis), was added to dissolve the peptide-containing solid. The side chains were deprotected during cleavage. After cleavage for about 2 hours, the solution was precipitated with 1200 mL (i.e. 10 mL per ml of the filtrate) of diethyl ether and sediment is collected by filtration. The sediment is dried by vacuum for about 2 hours. Finally, 4.28 g of crude title compound was got.

MS: m/z 1318.5

Analysis showed a target peak that was eluted at 10.509 minutes with the expected molecular weight (MS: m/z 1318.2). The purity was 70.476%.

4.2 g of the crude product was then purified as described in Example 1 above to give 2.8 g of pure title compound after freeze-drying.

Example 8

Synthesis of Further Peptides IV

The following peptides were synthesised using essentially the same procedure as that described in Example 7 above, except that appropriate amino acids were used as appropriate in the relevant peptide coupling sequences:

```
(SEQ ID No: 40)
Ala-Lys-Pro-Ser-Tyr-Hyp-Hyp-Thr-Tyr-Lys-Dopamine;

(SEQ ID No: 45)
Ala-Lys-Pro-Ser-Tyr-Hyp-Hyp-Thr-DOPA-Lys-Dopamine;

(SEQ ID No: 47)
Ala-Lys-Pro-Ser-DOPA-Hyp-Hyp-Thr-DOPA-Lys-Dopamine;

(SEQ ID No: 51)
Ala-Lys-Pro-Ser-Tyr-Hyp-Thr-DOPA-Hyp-Lys-Dopamine;
and

(SEQ ID No: 53)
Ala-Lys-Pro-Ser-DOPA-Hyp-Thr-DOPA-Hyp-Lys-Dopamine;
```

The crude yields and purity, retention time, MS values and final yields from these peptide syntheses were as shown in Table 4 below.

TABLE 4

| SEQ ID No. | Crude amount | Crude purity | Retention time | MS | Final amount |
|---|---|---|---|---|---|
| 40 | 4.29 g | 70.392% | 10.393 | 1318.5 | 2.55 g |
| 45 | 4.31 g | 69.173% | 10.953 | 1334.4 | 2.34 g |

TABLE 4-continued

| SEQ ID No. | Crude amount | Crude purity | Retention time | MS | Final amount |
|---|---|---|---|---|---|
| 47 | 4.23 g | 70.822% | 10.106 | 1350.6 | 2.67 g |
| 51 | 4.33 g | 68.948% | 10.354 | 1334.5 | 2.66 g |
| 53 | 4.19 g | 69.532% | 10.739 | 1350.5 | 2.36 g |

Example 9

```
                                          (SEQ ID No: 55)
Lys-Ala-Lys-Pro-Ser-Tyr-Hyp-Hyp-Thr-Dopamine
and

                                          (SEQ ID NO: 58)
Lys-Ala-Lys-Pro-Ser-DOPA-Hyp-Hyp-Thr-Dopamine
```

The title compounds were synthesized, using essentially the same process as described in Example 7 above, using Thr as the first amino acid with Fmoc-Thr(tBu)-Wang resin and with appropriate amino acids being used in the appropriate peptide coupling sequences.

MS (SEQ ID No: 20): m/z is 1155.3 (SEQ ID No: 55)

MS (SEQ ID No: 26): m/z is 1171.3 (SEQ ID No: 58)

Example 10

```
                                   (SEQ_ID No: 12)
Lys-Ala-Lys-Hyp-Ser-Tyr-Hyp-Hyp-Thr-Tyr,

                                   (SEQ ID No: 16)
Lys-Ala-Lys-Hyp-Ser-DOPA-Hyp-Hyp-Thr-Tyr,

                                   (SEQ ID No: 13)
Lys-Ala-Lys-Pro-Ser-DOPA-Hyp-Hyp-Thr-Tyr
and

                                   (SEQ ID NO: 14)
Lys-Ala-Lys-Pro-Ser-Tyr-Hyp-Hyp-Thr-Tyr
```

The title compounds were synthesized, using essentially the same process as described in Example 1 above, using Tyr as the first amino acid with Fmoc-Tyr(tBu)-Wang resin and with appropriate amino acids being used in the appropriate peptide coupling sequences.

MS (SEQ ID No: 12): m/z is 1199.3 (SEQ ID No: 12)

MS (SEQ ID No: 26): m/z is 1215.3 (SEQ ID No: 16)

MS (SEQ ID No: 20): m/z is 1199.3 (SEQ ID No: 13)

MS (SEQ ID No: 26): m/z is 1183.3 (SEQ ID No: 14)

Example 11

General Method for the Preparation of Peptide Gel Formulations

Various gels comprising peptide compounds described above (e.g. SEQ ID Nos: 7, 39, 33, 34, 15, 58, 50, 22, 18, 32, etc.) were prepared by mixing an appropriate amount of the isolated peptide compound with methyl cellulose (2.5%), propanediol (11%), glycerol (11%). The pH was adjusted to 5.5 by adding acetic acid (pH regulator; 0 to 0.5 g). All excipients were obtained from Sinopharm Chemical Reagent Co., Ltd. The gels were made with water for injection.

Example 12

Mouse Ear Swelling Model

35 Health male BALB/c mice with 6-8 weeks old and average body weight of 18-25 g were supplied from Changzhou Cvens Experimental Animal Co., Ltd. and housed and cared for about 1 week prior to the experiment. The housing temperature was around 25 to 27° C. with 74% humidity, alternating 12-hour periods of light and darkness, and free access to food and water. The mice were randomly divided into 7 groups as described in Table 5 below, with 5 mice in each group.

TABLE 5

| Group | Drug concentration |
|---|---|
| Model | 1 |
| Dex cream | 10 μg/g |
| SEQ ID No: 58 | 0.5 mg/g |
| SEQ ID No: 50 | 0.5 mg/g |
| SEQ ID No: 22 | 0.5 mg/g |
| SEQ ID No: 18 | 0.5 mg/g |
| SEQ ID No: 32 | 0.5 mg/g |

Dexamethasone acetate cream (Dex cream; 5 mg/10 g (which means that there was 5 mg Dex contained in 10 g of the cream), Fuyuan Pharmaceutical Co. Ltd., Anhui, China) was used as positive control.

The left ear of each mouse was used as an autologous control. The right ear of each mouse was treated with the above compounds in the stated concentrations.

About 0.1 g of the various gels, and Dex cream were applied to the right ear of mice in each group, both inside and outside. The blank gel base was applied on the ears in the model groups. After 1 hour, 20 μL of xylene (Shanghai Aladdin Bio-Chem Technology Co., Ltd.) was applied to the same ear of each mouse.

The mice were sacrificed by cervical dislocation 40 minutes after xylene application. The left and right ears were cut off. An EMS skin biopsy punch with a diameter of 8 mm was used to take a piece of the ear from the same site on both ears. The weights were recorded, and the swelling rate was calculated as a percentage according to the following formula:

$$(\text{right ear weight} - \text{left ear weight})/\text{left ear weight} \times 100$$

The results are shown in Table 6 below.

TABLE 6

| | model | DEX | 15 | 58 | 50 | 22 | 18 |
|---|---|---|---|---|---|---|---|
| Swelling rate | 89% | 38% | 63% | 43% | 54% | 40% | 57% |
| SD | 0.17 | 0.18 | 0.14 | 0.21 | 0.09 | 0.17 | 0.15 |

The results showed that all peptides could eliminate the edema caused by inflammation. The anti-inflammatory effects of peptide compound SEQ ID Nos 58 och 22 were stronger than the other peptide compounds tested.

Example 13

Croton Oil-Induced Anal Swelling Model in Rats

A croton oil mixture was prepared by mixing one part distilled water, four parts of pyridine (Nanjing Chemical Reagent Co., Ltd.), five parts of ether (China Pharmaceutical Group Chemical Reagents Co., Ltd) and ten parts of 6% croton oil (Shanghai Yuanye Biotechnology Co., Ltd.) ether solution.

6-8 weeks old SD rats with average body weights of 180-220 g were supplied by Changzhou Cvens Experimental Animal Co. Ltd. (Changzhou, Jiangsu Province, China). Prior to any experiments being conducted, the rats were housed under standardized conditions (at a constant temperature or 22±2° C., with alternating 12-hour periods of light and darkness) and were fed on a standard mouse diet with water, for about a week.

80 rats (40 males and 40 females) were randomly divided into 8 groups, as in Table 7 below, with 10 rats in each group.

The dexamethasone acetate cream was prepared as described in Example 3 above.

TABLE 7

| Group | Treatment | Drug concentration | Volume (μL) |
|---|---|---|---|
| 1 | Normal saline (Sham) | / | 200 |
| 2 | Blank gel (Model) | / | 200 |
| 3 | Dexamethasone acetate (Dex) | commercially available cream | 200 |
| 4 | SEQ ID No: 7 gel (A) | 0.5 mg/g | 200 |
| 5 | SEQ ID No: 39 gel (B) | 0.5 mg/g | 200 |
| 6 | SEQ ID No: 33 gel (C) | 0.5 mg/g | 200 |
| 7 | SEQ ID No: 34 gel (D) | 0.5 mg/g | 200 |
| 8 | SEQ ID No: 15 gel (E) | 0.5 mg/g | 200 |

The rats were anesthetized by isoflurane (China Pharmaceutical Group Chemical Reagents Co., Ltd.) inhalation. 75% alcohol cotton ball was used to disinfect the skin around the anus. Then 0.16 mL croton oil mixture was dripped slowly on a cotton swab, and inserted 0.5 cm into the rat anus.

The rat was lifted to keep the head upwards (the position was maintained for 10 seconds), then the cotton swab was withdrawn, and the croton oil mixture was evenly applied to the surrounding skin. The sham group was given the same volume, but of olive oil instead.

One hour after modeling, rats in each group were treated according to Table 7. The positive control drug was Dexamethasone acetate cream (Fuyuan Pharmaceutical Co. Ltd., Anhui, China). The gels of each compound were prepared as described in Example 11. The drug was administered one a day, for three consecutive days.

200 μL of the corresponding drugs were drawn with 1 mL syringe (needle removed). The syringe was inserted into the anal canal and about 160 mL of the respective test substances was pushed about 1.5 cm into the anal canal. The remaining of the respective test substances was applied to the surrounding skin near the anus. The skin around the anus was held tightly for 1 minute to prevent drug discharge.

In the morning of the fourth day, 1% Evans blue (EB) was injected into the tail vein. 30 minutes later, the rats were sacrificed by cervical dislocation.

The rats were placed in the supine position on an anatomical plate and their abdomens were opened. The rectoanal tissues (15 mm in length) were isolated and weighed and the EB dye present in the tissue was extracted using 1 mL of formamide.

All samples were transferred to a 55° C. water bath or a heat block. Incubation for 24 hours extracted EB from the tissue. The formamide/EB mixture was centrifuged to pelletize any remaining tissue fragments. Absorbance was measured at 610 nm, using 500 μL of formamide as a blank.

The content of EB in rectal and anal tissues was calculate using amount (in ng) of EB extravasated per mg of tissue to evaluate vascular permeability. The results are shown in FIG. 1 and show that all the compounds could reduce inflammatory swelling caused by croton oil application, as indicated by the variation of EB content in the different treatments. A decrease of EB concentration was an indication of vascular permeability.

The invention claimed is:

1. A compound consisting of the amino acid sequence:

(SEQ ID NO: 3)

$Xaa_1$-$Xaa_2$-Lys-$Xaa_3$-Ser-$Xaa_5$-$Xaa_6$-$Xaa_7$-$Xaa_8$-$Xaa_9$-$Xaa_{10}$-$Xaa_{11}$ wherein:

$Xaa_1$ is selected from the group consisting of Lys, Ala and DOPA, optionally comprising an N-terminal 3,4-dihydrocinnamic acid (HCA) residue;

$Xaa_2$ is optional and selected from the group consisting of Lys, Ala and DOPA, $Xaa_3$ is 3Hyp, 4Hyp, 3,4diHyp, 3,5diHyp, 4,5diHyp, or Pro;

$Xaa_5$ is Tyr or DOPA;

$Xaa_6$ is Ser, Pro, 3Hyp, 4Hyp, 3,4diHyp, 3,5diHyp, or 4,5diHyp;

$Xaa_7$ is Thr;

each of $Xaa_8$ and $Xaa_9$ is optional and, when present, is selected from the group consisting of Lys, Ala, Pro, 3Hyp, 4Hyp, 3,4diHyp, 3,5diHyp, 4,5diHyp, Thr, DOPA and Tyr; and $Xaa_{10}$ is Lys; and $Xaa_{11}$ is absent, DOPA, or dopamine; and regioisomers, stereoisomers pharmaceutically-acceptable salts, or cosmetically-acceptable salts thereof.

2. The compound as claimed in claim 1, wherein $Xaa_{11}$ is absent.

3. The compound as claimed in claim 1, wherein $Xaa_3$ is Pro.

4. The compound as claimed in claim 1, wherein $Xaa_6$ is 3Hyp or 4Hyp.

5. The compound as claimed in claim 1, wherein $Xaa_1$-$Xaa_2$ is selected from the group consisting of HCA-Ala-, Ala, DOPA, Lys-Ala-, and DOPA-Ala-.

6. The compound as claimed in claim 1, wherein $Xaa_8$ and $Xaa_9$ are each independently selected from the group consisting of Ala, 3Hyp, 4Hyp, Pro, Thr, DOPA, and Tyr.

7. The compound as claimed in claim 6, wherein the 4-amino acid sequence of $Xaa_7$-$Xaa_8$-$Xaa_9$-$Xaa_{10}$ is selected from the group consisting of:

```
                                         (SEQ ID NO: 85)
-Thr-Tyr-Hyp-Lys- where Hyp is 3Hyp or 4Hyp,

                                         (SEQ ID NO: 86)
-Thr-DOPA-Hyp-Lys- where Hyp is 3Hyp or 4Hyp, and

                                         (SEQ ID NO: 87)
-Thr-Ala-Hyp-Lys- where Hyp is 3Hyp or 4Hyp.
```

8. The compound as claimed in claim 1, wherein the compound consists of

```
                                          (SEQ ID NO: 5)
DOPA-Lys-Pro-Ser-Tyr-Hyp-Thr-Ala-Hyp-Lys where
Hyp is 3Hyp or 4Hyp;

                                           (SEQ ID NO: 7)
DOPA-Ala-Lys-Pro-Ser-Tyr-Hyp-Thr-Tyr-Hyp-Lys
where Hyp is 3Hyp or 4Hyp;

                                           (SEQ ID NO: 9)
DOPA-Ala-Lys-Pro-Ser-Tyr-Hyp-Thr-DOPA-Hyp-Lys
where Hyp is 3Hyp or 4Hyp;

                                         (SEQ ID NO: 11)
DOPA-Ala-Lys-Pro-Ser-DOPA-Hyp-Thr-Tyr-Hyp-Lys
where Hyp is 3Hyp or 4Hyp;

                                         (SEQ ID NO: 17)
HCA-Ala-Lys-Pro-Ser-Tyr-Hyp-Thr-Tyr-Hyp-Lys where
Hyp is 3Hyp or 4Hyp;

                                          (SEQ ID NO: 18)
HCA-Ala-Lys-Pro-Ser-Tyr-Hyp-Thr-DOPA-Hyp-Lys
where Hyp is 3Hyp or 4Hyp;

                                         (SEQ ID NO: 19)
HCA-Ala-Lys-Pro-Ser-DOPA-Hyp-Thr-DOPA-Hyp-Lys
where Hyp is 3Hyp or 4Hyp;

                                         (SEQ ID NO: 23)
HCA-Ala-Lys-Pro-Ser-DOPA-Hyp-Thr-Tyr-Hyp-Lys
where Hyp is 3Hyp or 4Hyp;

                                         (SEQ ID NO: 25)
HCA-Lys-Pro-Ser-Tyr-Hyp-Thr-Ala-Hyp-Lys where
Hyp is 3Hyp or 4Hyp;

                                         (SEQ ID NO: 26)
HCA-Lys-Pro-Ser-DOPA-Hyp-Thr-Ala-Hyp-Lys where
Hyp is 3Hyp or 4Hyp;

                                         (SEQ ID NO: 28)
DOPA-Lys-Pro-Ser-DOPA-Hyp-Thr-Ala-Hyp-Lys where
Hyp is 3Hyp or 4Hyp;

                                          (SEQ ID NO: 30)
DOPA-Ala-Lys-Pro-Ser-DOPA-Hyp-Thr-DOPA-Hyp-Lys
where Hyp is 3Hyp or 4Hyp;

                                         (SEQ ID NO: 33)
Ala-Lys-Pro-Ser-Tyr-Hyp-Thr-Tyr-Hyp-Lys where Hyp
is 3Hyp or 4Hyp;
```

-continued

```
                                         (SEQ ID NO: 34)
Ala-Lys-Pro-Ser-Tyr-Hyp-Thr-DOPA-Hyp-Lys where
Hyp is 3Hyp or 4Hyp;

                                         (SEQ ID NO: 35)
Ala-Lys-Pro-Ser-DOPA-Hyp-Thr-Tyr-Hyp-Lys where
Hyp is 3Hyp or 4Hyp; or

                                         (SEQ ID NO: 36)
Ala-Lys-Pro-Ser-DOPA-Hyp-Thr-DOPA-Hyp-Lys where
Hyp is 3Hyp or 4Hyp.
```

9. The compound as claimed in claim 1, wherein $Xaa_1$-$Xaa_2$- is Ala or Lys-Ala.

10. The compound as claimed in claim 9, wherein the compound has the amino acid sequence:

```
                                         (SEQ ID NO: 38)
Ala-Lys-Pro-Ser-Tyr-Hyp-Thr-Tyr-Hyp-Lys-DOPA
where Hyp is 3Hyp or 4Hyp;

                                         (SEQ ID NO: 39)
Ala-Lys-Pro-Ser-Tyr-Hyp-Thr-Tyr-Hyp-Lys-Dopamine
where Hyp is 3Hyp or 4Hyp;

                                         (SEQ ID NO: 48)
where Ala-Lys-Pro-Ser-Tyr-Hyp-Thr-DOPA-Hyp-Lys-
DOPA Hyp is 3Hyp or 4Hyp;

                                         (SEQ ID NO: 49)
Ala-Lys-Pro-Ser-DOPA-Hyp-Thr-Tyr-Hyp-Lys-DOPA
where Hyp is 3Hyp or 4Hyp;

                                         (SEQ ID NO: 50)
Ala-Lys-Pro-Ser-DOPA-Hyp-Thr-DOPA-Hyp-Lys-DOPA
where Hyp is 3Hyp or 4Hyp;

                                         (SEQ ID NO: 51)
Ala-Lys-Pro-Ser-Tyr-Hyp-Thr-DOPA-Hyp-Lys-Dopamine
where Hyp is 3Hyp or 4Hyp;

                                         (SEQ ID NO: 52)
Ala-Lys-Pro-Ser-DOPA-Hyp-Thr-Tyr-Hyp-Lys-Dopamine
where Hyp is 3Hyp or 4Hyp; or

                                          (SEQ ID NO: 53)
Ala-Lys-Pro-Ser-DOPA-Hyp-Thr-DOPA-Hyp-Lys-Dopamine
where Hyp is 3Hyp or 4Hyp.
```

11. The compound as claimed in claim 1, wherein:

$Xaa_1$ is Ala;

$Xaa_2$ is absent;

$Xaa_3$ is Pro;

$Xaa_6$ is is Pro; and/or $Xaa_7$-$Xaa_8$-$Xaa_9$-$Xaa_{10}$ is selected from the group consisting of

```
                         (SEQ ID NO: 80)
-Thr-Tyr-Pro-Lys-, and

                         (SEQ ID NO: 81)
-Thr-DOPA-Pro-Lys-,
```

$Xaa_{11}$ is absent.

12. A pharmaceutical formulation comprising a compound of claim 1 and a pharmaceutically- or cosmetically-acceptable, adjuvant, diluent or carrier.

13. The pharmaceutical formulation as claimed in claim 12, wherein the pharmaceutically- or cosmetically-acceptable adjuvant, diluent or carrier is a topical adjuvant, diluent or carrier.

14. The pharmaceutical formulation as claimed in claim 13, which is in the form of a gel, a spray, a cream, an ointment or a dry powder.

15. A method of treatment of inflammation, an inflammatory disorder, and/or of a disorder characterised by inflammation, which method comprises the administration of a compound as defined in claim 1 to a patient in need of such treatment.

16. The method as claimed in claim 15, wherein the disorder characterised by inflammation is, or results in, a wound or a burn.

17. The method as claimed in claim 16, wherein the disorder resulting in a wound is haemorrhoids or ulcerative colitis.

18. The method as claimed in claim 15, wherein the compound(s) or salt thereof is administered topically in the form of a topical formulation.

19. The method as claimed in claim 18 wherein the relevant condition is treated by way of direct topical administration to the skin or to a mucosal surface.

20. The method as claimed in claim 15, wherein the compound(s) is/are administered by oral, intravenous, cutaneous or subcutaneous, nasal, intramuscular, intraperitoneal, pulmonary or anorectal delivery.

* * * * *

SEQUENCE LISTING

```
<160> NUMBER OF SEQ ID NOS: 89

<210> SEQ ID NO 1
<211> LENGTH: 10
<212> TYPE: PRT
<213> ORGANISM: Mytilus sp.
<220> FEATURE:
<223> OTHER INFORMATION: mefp1- tandem repeat decapeptide
<220> FEATURE:
<221> NAME/KEY: SITE
<222> LOCATION: 6,7
<223> OTHER INFORMATION: Wherein Xaa is 3-hydroxyproline or
      4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 1

Ala Lys Pro Ser Tyr Xaa Xaa Thr Xaa Lys
1               5                   10


<210> SEQ ID NO 2
<211> LENGTH: 10
<212> TYPE: PRT
<213> ORGANISM: Mytilus sp.
<220> FEATURE:
<223> OTHER INFORMATION: Decapeptide analogue
```

-continued

<220> FEATURE:
<221> NAME/KEY: SITE
<222> LOCATION: 6,7
<223> OTHER INFORMATION: Wherein Xaa is 3-hydroxyproline or
4-hydroxyproline

<400> SEQUENCE: 2

Ala Lys Pro Ser Tyr Xaa Xaa Thr Tyr Lys
1 5 10

<210> SEQ ID NO 3
<211> LENGTH: 13
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is optionally N-terminally modified
with a 3,4-dihydrocinnamic acid group, or is not so modified
<220> FEATURE:
<223> OTHER INFORMATION: Peptide compound
<220> FEATURE:
<221> NAME/KEY: VARIANT
<222> LOCATION: 1
<223> OTHER INFORMATION: Wherein Xaa is selected from the group lysine,
alanine and 3,4-dihydroxyphenylalanine
<220> FEATURE:
<221> NAME/KEY: VARIANT
<222> LOCATION: 2
<223> OTHER INFORMATION: Wherein Xaa is selected from the group lysine,
alanine and 3,4-dihydroxyphenylalanine, or is absent
<220> FEATURE:
<221> NAME/KEY: VARIANT
<222> LOCATION: 4
<223> OTHER INFORMATION: Wherein Xaa is proline, 3-hydroxyproline,
4-hydroxyproline, 5-hydroxyproline, 3,4-dihydroxyproline,
3,5-dihydroxyproline, or 4,5-dihydroxyproline
<220> FEATURE:
<221> NAME/KEY: VARIANT
<222> LOCATION: 6
<223> OTHER INFORMATION: Wherein Xaa is tyrosine or
3,4-dihydroxyphenylalanine
<220> FEATURE:
<221> NAME/KEY: VARIANT
<222> LOCATION: 7
<223> OTHER INFORMATION: Wherein Xaa is serine, proline,
3-hydroxyproline, 4-hydroxyproline, 5-hydroxyproline,
3,4-dihydroxyproline, 3,5-dihydroxyproline, or
4,5-dihydroxyproline
<220> FEATURE:
<221> NAME/KEY: VARIANT
<222> LOCATION: 8
<223> OTHER INFORMATION: Wherein Xaa is selected from the group lysine,
alanine, proline, 3-hydroxyproline, 4-hydroxyproline,
5-hydroxyproline, 3,4-dihydroxyproline, 3,5-dihydroxyproline,
4,5-dihydroxyproline, threonine, 3,4-dihydroxyphenylalanine, and
tyrosine
<220> FEATURE:
<221> NAME/KEY: VARIANT
<222> LOCATION: 9..12
<223> OTHER INFORMATION: Wherein Xaa is selected from the group lysine,
alanine, proline, 3-hydroxyproline, 4-hydroxyproline,
5-hydroxyproline, 3,4-dihydroxyproline, 3,5-dihydroxyproline,
4,5-dihydroxyproline, threonine, 3,4-dihydroxyphenylalanine, and
tyrosine, or is absent
<220> FEATURE:
<221> NAME/KEY: VARIANT
<222> LOCATION: 13
<223> OTHER INFORMATION: Wherein Xaa is absent or is
3,4-dihydroxyphenylalanine, dopamine, or a dopamine fragment

<400> SEQUENCE: 3

Xaa Xaa Lys Xaa Ser Xaa Xaa Xaa Xaa Xaa Xaa Xaa Xaa
1 5 10

-continued

```
<210> SEQ ID NO 4
<211> LENGTH: 13
<212> TYPE: PRT
<213> ORGANISM: Artificial Sequence
<220> FEATURE:
<221> NAME/KEY: SITE
<222> LOCATION: 1
<223> OTHER INFORMATION: Wherein where Xaa at position 1 is alanine or
      lysine, Xaa is N-terminally modified with a 3,4-dihydrocinnamic
      acid group
<220> FEATURE:
<223> OTHER INFORMATION: Peptide compound
<220> FEATURE:
<221> NAME/KEY: VARIANT
<222> LOCATION: 1..3
<223> OTHER INFORMATION: Wherein Xaa Xaa Xaa is selected from:
      i) alanine at position 1 and no amino acid at positions 2 and 3;
      ii) lysine at position 1 and no amino acid at positions 2 and 3;
      iii) lysine at position 1, alanine at position 2 and no amino
      acid at position 3; iv) 3,4- dihydroxyphenylalanine at position
      1, lysine at position 2 and no amino acid at position 3; v)
      dihydroxyphenylalanine at position 1, lysine at position 2 and
      alanine at position 3; vi) dihydroxyphenylalanine at position 1
      and no amino acid at positions 2 and 3; or vii)
      dihydroxyphenylalanine at position 1, alanine at position 2 and
      no amino acid at position 3
<220> FEATURE:
<221> NAME/KEY: SITE
<222> LOCATION: 4
<223> OTHER INFORMATION: Wherein where Xaa Xaa Xaa at positions 1..3 is
      no amino acid, Lys is N-terminally modified with a
      3,4-dihydrocinnamic acid group
<220> FEATURE:
<221> NAME/KEY: VARIANT
<222> LOCATION: 5
<223> OTHER INFORMATION: Wherein Xaa represents proline,
      3-hydroxyproline, 4-hydroxyproline, 5-hydroxyproline,
      3,4-dihydroxyproline, 3,5-dihydroxyproline, or
      4,5-dihydroxyproline
<220> FEATURE:
<221> NAME/KEY: VARIANT
<222> LOCATION: 7
<223> OTHER INFORMATION: Wherein Xaa represents tyrosine or
      3,4-dihydroxyphenylalanine
<220> FEATURE:
<221> NAME/KEY: VARIANT
<222> LOCATION: 8
<223> OTHER INFORMATION: Wherein Xaa represents serine, proline,
      3-hydroxyproline, 4-hydroxyproline, 5-hydroxyproline,
      3,4-dihydroxyproline, 3,5-dihydroxyproline, or
      4,5-dihydroxyproline
<220> FEATURE:
<221> NAME/KEY: VARIANT
<222> LOCATION: 9
<223> OTHER INFORMATION: Wherein Xaa is selected from the group lysine,
      alanine, proline, 3-hydroxyproline, 4-hydroxyproline,
      5-hydroxyproline, 3,4-dihydroxyproline, 3,5-dihydroxyproline,
      4,5-dihydroxyproline, threonine, 3,4-dihydroxyphenylalanine and
      tyrosine
<220> FEATURE:
<221> NAME/KEY: VARIANT
<222> LOCATION: 10..13
<223> OTHER INFORMATION: Wherein Xaa is selected from the group lysine,
      alanine, proline, 3-hydroxyproline, 4-hydroxyproline,
      5-hydroxyproline, 3,4-dihydroxyproline, 3,5-dihydroxyproline,
      4,5-dihydroxyproline, threonine, 3,4-dihydroxyphenylalanine and
      tyrosine, or is absent

<400> SEQUENCE: 4

Xaa Xaa Xaa Lys Xaa Ser Xaa Xaa Xaa Xaa Xaa Xaa Xaa
1               5                   10


<210> SEQ ID NO 5
<211> LENGTH: 10
<212> TYPE: PRT
<213> ORGANISM: Artificial Sequence
<220> FEATURE:
```

<221> NAME/KEY: SITE
<222> LOCATION: 1
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline,
4-hydroxyproline, or 5-hydroxyproline

<400> SEQUENCE: 5

Xaa Lys Pro Ser Tyr Xaa Thr Ala Xaa Lys
1 5 10

<210> SEQ ID NO 6
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 6,7
<223> OTHER INFORMATION: Wherein Xaa is 3-hydroxyproline,
4-hydroxyproline, or 5-hydroxyproline

<400> SEQUENCE: 6

Xaa Lys Pro Ser Tyr Xaa Thr Ala Xaa Lys
1 5 10

<210> SEQ ID NO 7
<211> LENGTH: 11
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,10
<223> OTHER INFORMATION: Wherein Xaa is 3-hydroxyproline,
4-hydroxyproline, or 5-hydroxyproline

<400> SEQUENCE: 7

Xaa Ala Lys Pro Ser Tyr Xaa Thr Tyr Xaa Lys
1 5 10

<210> SEQ ID NO 8
<211> LENGTH: 11
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,8
<223> OTHER INFORMATION: Wherein Xaa is 3-hydroxyproline,
4-hydroxyproline, or 5-hydroxyproline

<400> SEQUENCE: 8

Xaa Ala Lys Pro Ser Tyr Xaa Xaa Thr Tyr Lys
1 5 10

<210> SEQ ID NO 9
<211> LENGTH: 11
<212> TYPE: PRT
<213> ORGANISM: Artificial Sequence
<220> FEATURE:
<221> NAME/KEY: SITE
<222> LOCATION: 1,9
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,10
<223> OTHER INFORMATION: Wherein Xaa is 3-hydroxyproline, 4-hydroxyproline, or 5-hydroxyproline

<400> SEQUENCE: 9

Xaa Ala Lys Pro Ser Tyr Xaa Thr Xaa Xaa Lys
1 5 10

<210> SEQ ID NO 10
<211> LENGTH: 11
<212> TYPE: PRT
<213> ORGANISM: Artificial Sequence
<220> FEATURE:
<221> NAME/KEY: SITE
<222> LOCATION: 1,10
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,8
<223> OTHER INFORMATION: Wherein Xaa is 3-hydroxyproline, 4-hydroxyproline, or 5-hydroxyproline

<400> SEQUENCE: 10

Xaa Ala Lys Pro Ser Tyr Xaa Xaa Thr Xaa Lys
1 5 10

<210> SEQ ID NO 11
<211> LENGTH: 11
<212> TYPE: PRT
<213> ORGANISM: Artificial Sequence
<220> FEATURE:
<221> NAME/KEY: SITE
<222> LOCATION: 1,6
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,10
<223> OTHER INFORMATION: Wherein Xaa is 3-hydroxyproline, 4-hydroxyproline, or 5-hydroxyproline

<400> SEQUENCE: 11

Xaa Ala Lys Pro Ser Xaa Xaa Thr Tyr Xaa Lys
1 5 10

<210> SEQ ID NO 12
<211> LENGTH: 9
<212> TYPE: PRT
<213> ORGANISM: Artificial Sequence
<220> FEATURE:
<221> NAME/KEY: SITE -continued

```
<222> LOCATION: 1
<223> OTHER INFORMATION: Wherein Lys is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 5,6
<223> OTHER INFORMATION: Wherein Xaa is 3-hydroxyproline,
      4-hydroxyproline, or 5-hydroxyproline

<400> SEQUENCE: 12

Lys Pro Ser Tyr Xaa Xaa Thr Ala Lys
1               5


<210> SEQ ID NO 13
<211> LENGTH: 8
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound

<400> SEQUENCE: 13

Ala Lys Pro Ser Tyr Thr Tyr Lys
1               5


<210> SEQ ID NO 14
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 14

Ala Lys Pro Ser Tyr Xaa Thr Xaa Xaa Lys
1               5                   10


<210> SEQ ID NO 15
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 5,8
<223> OTHER INFORMATION: Wherein Xaa is 3,4-dihydroxyphenylalanine
<220> FEATURE:
<221> NAME/KEY: SITE
```

```
<222> LOCATION: 6,9
<223> OTHER INFORMATION: Wherein Xaa is 3-hydroxyproline,
      4-hydroxyproline, or 5-hydroxyproline

<400> SEQUENCE: 15

Ala Lys Pro Ser Xaa Xaa Thr Xaa Xaa Lys
1               5                   10


<210> SEQ ID NO 16
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 16

Ala Lys Pro Ser Tyr Xaa Xaa Thr Tyr Lys
1               5                   10


<210> SEQ ID NO 17
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 17

Ala Lys Pro Ser Tyr Xaa Xaa Thr Xaa Lys
1               5                   10


<210> SEQ ID NO 18
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 5,9
<223> OTHER INFORMATION: Wherein Xaa is 3,4-dihydroxyphenylalanine
<220> FEATURE:
```

```
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 18

Ala Lys Pro Ser Xaa Xaa Xaa Thr Xaa Lys
1               5                   10


<210> SEQ ID NO 19
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 19

Ala Lys Pro Ser Xaa Xaa Thr Tyr Xaa Lys
1               5                   10


<210> SEQ ID NO 20
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Wherein Ala is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 20

Ala Lys Pro Ser Xaa Xaa Xaa Thr Tyr Lys
1               5                   10


<210> SEQ ID NO 21
<211> LENGTH: 9
<212> TYPE: PRT
<213> ORGANISM: Artificial Sequence
<220> FEATURE:
<221> NAME/KEY: SITE
<222> LOCATION: 1
<223> OTHER INFORMATION: Wherein Lys is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 5,8
```

<223> OTHER INFORMATION: Wherein Xaa is 3-hydroxyproline,
      4-hydroxyproline, or 5-hydroxyproline

<400> SEQUENCE: 21

Lys Pro Ser Tyr Xaa Thr Ala Xaa Lys
1               5

<210> SEQ ID NO 22
<211> LENGTH: 9
<212> TYPE: PRT
<213> ORGANISM: Artificial Sequence
<220> FEATURE:
<221> NAME/KEY: SITE
<222> LOCATION: 1
<223> OTHER INFORMATION: Wherein Lys is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 4
<223> OTHER INFORMATION: Wherein Xaa is 3,4-dihydroxyphenylalanine
<220> FEATURE:
<221> NAME/KEY: SITE
<222> LOCATION: 5,8
<223> OTHER INFORMATION: Wherein Xaa is 3-hydroxyproline,
      4-hydroxyproline, or 5-hydroxyproline

<400> SEQUENCE: 22

Lys Pro Ser Xaa Xaa Thr Ala Xaa Lys
1               5

<210> SEQ ID NO 23
<211> LENGTH: 9
<212> TYPE: PRT
<213> ORGANISM: Artificial Sequence
<220> FEATURE:
<221> NAME/KEY: SITE
<222> LOCATION: 1
<223> OTHER INFORMATION: Wherein Lys is N-terminally modified with a
      3,4-dihydrocinnamic acid residue
<220> FEATURE:
<223> OTHER INFORMATION: Peptide compound
<220> FEATURE:
<221> NAME/KEY: SITE
<222> LOCATION: 4
<223> OTHER INFORMATION: Wherein Xaa is 3,4-dihydroxyphenylalanine
<220> FEATURE:
<221> NAME/KEY: SITE
<222> LOCATION: 5,6
<223> OTHER INFORMATION: Wherein Xaa is 3-hydroxyproline,
      4-hydroxyproline, or 5-hydroxyproline

<400> SEQUENCE: 23

Lys Pro Ser Xaa Xaa Xaa Thr Ala Lys
1               5

<210> SEQ ID NO 24
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 4,7,8
<223> OTHER INFORMATION: Wherein Xaa is 3-hydroxyproline,
      4-hydroxyproline, or 5-hydroxyproline

<400> SEQUENCE: 24

Lys Ala Lys Xaa Ser Tyr Xaa Xaa Thr Tyr
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6
<223> OTHER INFORMATION: Wherein Xaa is 3,4-dihydroxyphenylalanine
<220> FEATURE:
<221> NAME/KEY: SITE
<222> LOCATION: 7,8
<223> OTHER INFORMATION: Wherein Xaa is 3-hydroxyproline,
4-hydroxyproline, or 5-hydroxyproline

<400> SEQUENCE: 25

```
Lys Ala Lys Pro Ser Xaa Xaa Xaa Thr Tyr
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 7,8
<223> OTHER INFORMATION: Wherein Xaa is 3-hydroxyproline,
4-hydroxyproline, or 5-hydroxyproline

<400> SEQUENCE: 26

```
Lys Ala Lys Pro Ser Tyr Xaa Xaa Thr Tyr
1               5                   10
```

<210> SEQ ID NO 27
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 4,7,8
<223> OTHER INFORMATION: Wherein Xaa is 3-hydroxyproline,
4-hydroxyproline, or 5-hydroxyproline
<220> FEATURE:
<221> NAME/KEY: SITE
<222> LOCATION: 6
<223> OTHER INFORMATION: Wherein Xaa is 3,4-dihydroxyphenylalanine

<400> SEQUENCE: 27

```
Lys Ala Lys Xaa Ser Xaa Xaa Xaa Thr Tyr
1               5                   10
```

<210> SEQ ID NO 28
<211> LENGTH: 10
<212> TYPE: PRT
<213> ORGANISM: Artificial Sequence
<220> FEATURE:
<221> NAME/KEY: SITE
<222> LOCATION: 1,5
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline,
4-hydroxyproline, or 5-hydroxyproline

<400> SEQUENCE: 28

Xaa Lys Pro Ser Xaa Xaa Thr Ala Xaa Lys
1 5 10

<210> SEQ ID NO 29
<211> LENGTH: 10
<212> TYPE: PRT
<213> ORGANISM: Artificial Sequence
<220> FEATURE:
<221> NAME/KEY: SITE
<222> LOCATION: 1,5
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 6,7
<223> OTHER INFORMATION: Wherein Xaa is 3-hydroxyproline,
4-hydroxyproline, or 5-hydroxyproline

<400> SEQUENCE: 29

Xaa Lys Pro Ser Xaa Xaa Xaa Thr Ala Lys
1 5 10

<210> SEQ ID NO 30
<211> LENGTH: 11
<212> TYPE: PRT
<213> ORGANISM: Artificial Sequence
<220> FEATURE:
<221> NAME/KEY: SITE
<222> LOCATION: 1,6,9
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,10
<223> OTHER INFORMATION: Wherein Xaa is 3-hydroxyproline,
4-hydroxyproline, or 5-hydroxyproline

<400> SEQUENCE: 30

Xaa Ala Lys Pro Ser Xaa Xaa Thr Xaa Xaa Lys
1 5 10

<210> SEQ ID NO 31
<211> LENGTH: 11
<212> TYPE: PRT
<213> ORGANISM: Artificial Sequence
<220> FEATURE:
<221> NAME/KEY: SITE
<222> LOCATION: 1,6
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,8
<223> OTHER INFORMATION: Wherein Xaa is 3-hydroxyproline,
4-hydroxyproline, or 5-hydroxyproline

<400> SEQUENCE: 31

Xaa Ala Lys Pro Ser Xaa Xaa Xaa Thr Tyr Lys
1 5 10

<210> SEQ ID NO 32
<211> LENGTH: 11
<212> TYPE: PRT
<213> ORGANISM: Artificial Sequence
<220> FEATURE:
<221> NAME/KEY: SITE

```
<222> LOCATION: 1,6,10
<223> OTHER INFORMATION: Wherein Xaa is 3,4-dihydroxyphenylalanine
<220> FEATURE:
<223> OTHER INFORMATION: Peptide compound
<220> FEATURE:
<221> NAME/KEY: SITE
<222> LOCATION: 7,8
<223> OTHER INFORMATION: Wherein Xaa is 3-hydroxyproline,
      4-hydroxyproline, or 5-hydroxyproline

<400> SEQUENCE: 32

Xaa Ala Lys Pro Ser Xaa Xaa Xaa Thr Xaa Lys
1               5                   10


<210> SEQ ID NO 33
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 33

Ala Lys Pro Ser Tyr Xaa Thr Tyr Xaa Lys
1               5                   10


<210> SEQ ID NO 34
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 34

Ala Lys Pro Ser Tyr Xaa Thr Xaa Xaa Lys
1               5                   10


<210> SEQ ID NO 35
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline

<400> SEQUENCE: 35

Ala Lys Pro Ser Xaa Xaa Thr Tyr Xaa Lys
1               5                   10


<210> SEQ ID NO 36
```

<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,8
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline,
4-hydroxyproline, or 5-hydroxyproline

<400> SEQUENCE: 36

Ala Lys Pro Ser Xaa Xaa Thr Xaa Xaa Lys
1 5 10

<210> SEQ ID NO 37
<211> LENGTH: 13
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is optionally N-terminally modified
with a 3,4-dihydrocinnamic acid residue, or is no so modified
<220> FEATURE:
<223> OTHER INFORMATION: Peptide compound
<220> FEATURE:
<221> NAME/KEY: VARIANT
<222> LOCATION: 1
<223> OTHER INFORMATION: Wherein Xaa is selected from the group lysine,
alanine and 3,4-dihydroxyphenylalanine
<220> FEATURE:
<221> NAME/KEY: VARIANT
<222> LOCATION: 2
<223> OTHER INFORMATION: Wherein Xaa is selected from the group lysine,
alanine and 3,4-dihydroxyphenylalanine, or is absent
<220> FEATURE:
<221> NAME/KEY: VARIANT
<222> LOCATION: 6
<223> OTHER INFORMATION: Wherein Xaa represents tyrosine or
3,4-dihydroxyphenylalanine
<220> FEATURE:
<221> NAME/KEY: VARIANT
<222> LOCATION: 7
<223> OTHER INFORMATION: Wherein Xaa represents serine, proline,
3-hydroxyproline, 4-hydroxyproline, 5-hydroxyproline,
3,4-dihydroxyproline, 3,5-dihydroxyproline, or
4,5-dihydroxyproline
<220> FEATURE:
<221> NAME/KEY: VARIANT
<222> LOCATION: 8
<223> OTHER INFORMATION: Wherein Xaa is selected from the group lysine,
alanine, proline, 3-hydroxyproline, 4-hydroxyproline,
5-hydroxyproline, 3,4-dihydroxyproline, 3,5-dihydroxyproline,
4,5-dihydroxyproline, threonine, 3,4-dihydroxyphenylalanine and
tyrosine
<220> FEATURE:
<221> NAME/KEY: VARIANT
<222> LOCATION: 9..12
<223> OTHER INFORMATION: Wherein Xaa is selected from the group lysine,
alanine, proline, 3-hydroxyproline, 4-hydroxyproline,
5-hydroxyproline, 3,4-dihydroxyproline, 3,5-dihydroxyproline,
4,5-dihydroxyproline, threonine, 3,4-dihydroxyphenylalanine and
tyrosine, or is absent
<220> FEATURE:
<221> NAME/KEY: VARIANT
<222> LOCATION: 13
<223> OTHER INFORMATION: Wherein Xaa is represents
3,4-dihydroxyphenylalanine or dopamine or a dopamine fragment, or
is absent

<400> SEQUENCE: 37

Xaa Xaa Lys Pro Ser Xaa Xaa Xaa Xaa Xaa Xaa Xaa Xaa
1 5 10

<210> SEQ ID NO 38
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 11
<223> OTHER INFORMATION: Wherein Xaa is 3,4-dihydroxyphenylalanine

<400> SEQUENCE: 38

Ala Lys Pro Ser Tyr Xaa Thr Tyr Xaa Lys Xaa
1 5 10

<210> SEQ ID NO 39
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 11
<223> OTHER INFORMATION: Wherein Xaa is dopamine

<400> SEQUENCE: 39

Ala Lys Pro Ser Tyr Xaa Thr Tyr Xaa Lys Xaa
1 5 10

<210> SEQ ID NO 40
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,7
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 11
<223> OTHER INFORMATION: Wherein Xaa is dopamine

<400> SEQUENCE: 40

Ala Lys Pro Ser Tyr Xaa Xaa Thr Tyr Lys Xaa
1 5 10

<210> SEQ ID NO 41
<211> LENGTH: 11
<212> TYPE: PRT
<213> ORGANISM: Artificial Sequence
<220> FEATURE:
<223> OTHER INFORMATION: Peptide compound

```
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 11
<223> OTHER INFORMATION: Wherein Xaa is 3,4-dihydroxyphenylalanine

<400> SEQUENCE: 41

Ala Lys Pro Ser Tyr Xaa Xaa Thr Tyr Lys Xaa
1               5                   10


<210> SEQ ID NO 42
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 9,11
<223> OTHER INFORMATION: Wherein Xaa is 3,4-dihydroxyphenylalanine

<400> SEQUENCE: 42

Ala Lys Pro Ser Tyr Xaa Xaa Thr Xaa Lys Xaa
1               5                   10


<210> SEQ ID NO 43
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,11
<223> OTHER INFORMATION: Wherein Xaa is 3,4-dihydroxyphenylalanine
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline

<400> SEQUENCE: 43

Ala Lys Pro Ser Xaa Xaa Xaa Thr Tyr Lys Xaa
1               5                   10


<210> SEQ ID NO 44
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,9,11
<223> OTHER INFORMATION: Wherein Xaa is 3,4-dihydroxyphenylalanine
<220> FEATURE:
<221> NAME/KEY: SITE
<222> LOCATION: 6,7
<223> OTHER INFORMATION: Wherein Xaa is 3-hydroxyproline,
      4-hydroxyproline, or 5-hydroxyproline
```

<400> SEQUENCE: 44

Ala Lys Pro Ser Xaa Xaa Xaa Thr Xaa Lys Xaa
1 5 10

<210> SEQ ID NO 45
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,7
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine
<220> FEATURE:
<221> NAME/KEY: SITE
<222> LOCATION: 11
<223> OTHER INFORMATION: Wherein Xaa is dopamine

<400> SEQUENCE: 45

Ala Lys Pro Ser Tyr Xaa Xaa Thr Xaa Lys Xaa
1 5 10

<210> SEQ ID NO 46
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine
<220> FEATURE:
<221> NAME/KEY: SITE
<222> LOCATION: 6,7
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 11
<223> OTHER INFORMATION: Wherein Xaa is dopamine

<400> SEQUENCE: 46

Ala Lys Pro Ser Xaa Xaa Xaa Thr Tyr Lys Xaa
1 5 10

<210> SEQ ID NO 47
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,9
<223> OTHER INFORMATION: Wherein Xaa is 3,4-dihydroxyphenylalanine
<220> FEATURE:
<221> NAME/KEY: SITE
<222> LOCATION: 6,7
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 11
<223> OTHER INFORMATION: Wherein Xaa is dopamine

<400> SEQUENCE: 47

Ala Lys Pro Ser Xaa Xaa Xaa Thr Xaa Lys Xaa
1 5 10

<210> SEQ ID NO 48
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,9
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 8,11
<223> OTHER INFORMATION: Wherein Xaa is 3,4-dihydroxyphenylalanine

<400> SEQUENCE: 48

Ala Lys Pro Ser Tyr Xaa Thr Xaa Xaa Lys Xaa
1 5 10

<210> SEQ ID NO 49
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,11
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline, 4-hydroxyproline, or 5-hydroxyproline

<400> SEQUENCE: 49

Ala Lys Pro Ser Xaa Xaa Thr Tyr Xaa Lys Xaa
1 5 10

<210> SEQ ID NO 50
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,8,11
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline, 4-hydroxyproline, or 5-hydroxyproline

<400> SEQUENCE: 50

Ala Lys Pro Ser Xaa Xaa Thr Xaa Xaa Lys Xaa
1 5 10

<210> SEQ ID NO 51
<211> LENGTH: 11
<212> TYPE: PRT
<213> ORGANISM: Artificial Sequence
<220> FEATURE:
<223> OTHER INFORMATION: Peptide compound
<220> FEATURE:

<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 8
<223> OTHER INFORMATION: Wherein Xaa is 3,4-dihydroxyphenylalanine
<220> FEATURE:
<221> NAME/KEY: SITE
<222> LOCATION: 11
<223> OTHER INFORMATION: Wherein Xaa is dopamine

<400> SEQUENCE: 51

Ala Lys Pro Ser Tyr Xaa Thr Xaa Xaa Lys Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 11
<223> OTHER INFORMATION: Wherein Xaa is dopamine

<400> SEQUENCE: 52

Ala Lys Pro Ser Xaa Xaa Thr Tyr Xaa Lys Xaa
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,8
<223> OTHER INFORMATION: Wherein Xaa is 3,4-dihydroxyphenylalanine
<220> FEATURE:
<221> NAME/KEY: SITE
<222> LOCATION: 6,9
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 11
<223> OTHER INFORMATION: Wherein Xaa is dopamine

<400> SEQUENCE: 53

Ala Lys Pro Ser Xaa Xaa Thr Xaa Xaa Lys Xaa
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE

```
<222> LOCATION: 7,8
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 10
<223> OTHER INFORMATION: Wherein Xaa is 3,4-dihydroxyphenylalanine

<400> SEQUENCE: 54

Lys Ala Lys Pro Ser Tyr Xaa Xaa Thr Xaa
1               5                   10


<210> SEQ ID NO 55
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 7,8
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 10
<223> OTHER INFORMATION: Wherein Xaa is dopamine

<400> SEQUENCE: 55

Lys Ala Lys Pro Ser Tyr Xaa Xaa Thr Xaa
1               5                   10


<210> SEQ ID NO 56
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 4,7,8
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 10
<223> OTHER INFORMATION: Wherein Xaa is 3,4-dihydroxyphenylalanine

<400> SEQUENCE: 56

Lys Ala Lys Xaa Ser Tyr Xaa Xaa Thr Xaa
1               5                   10


<210> SEQ ID NO 57
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6,10
<223> OTHER INFORMATION: Wherein Xaa is 3,4-dihydroxyphenylalanine
<220> FEATURE:
<221> NAME/KEY: SITE
<222> LOCATION: 7,8
<223> OTHER INFORMATION: Wherein Xaa is 3-hydroxyproline,
      4-hydroxyproline, or 5-hydroxyproline

<400> SEQUENCE: 57

Lys Ala Lys Pro Ser Xaa Xaa Xaa Thr Xaa
1               5                   10
```

<210> SEQ ID NO 58
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6
<223> OTHER INFORMATION: Wherein Xaa is 3,4-dihydroxyphenylalanine
<220> FEATURE:
<221> NAME/KEY: SITE
<222> LOCATION: 7,8
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 10
<223> OTHER INFORMATION: Wherein Xaa is dopamine

<400> SEQUENCE: 58

Lys Ala Lys Pro Ser Xaa Xaa Xaa Thr Xaa
1 5 10

<210> SEQ ID NO 59
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 4,7,8
<223> OTHER INFORMATION: Wherein Xaa is 3-hydroxyproline, 4-hydroxyproline, or 5-hydroxyproline
<220> FEATURE:
<221> NAME/KEY: SITE
<222> LOCATION: 6,10
<223> OTHER INFORMATION: Wherein Xaa is 3,4-dihydroxyphenylalanine

<400> SEQUENCE: 59

Lys Ala Lys Xaa Ser Xaa Xaa Xaa Thr Xaa
1 5 10

<210> SEQ ID NO 60
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 60

Ala Lys Pro Ser Tyr Pro Pro Thr Xaa Lys
1 5 10

<210> SEQ ID NO 61
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine

<400> SEQUENCE: 61

Ala Lys Pro Ser Xaa Pro Pro Thr Tyr Lys
1 5 10

<210> SEQ ID NO 62
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5,9
<223> OTHER INFORMATION: Wherein Xaa is 3,4-dihydroxyphenylalanine

<400> SEQUENCE: 62

Ala Lys Pro Ser Xaa Pro Pro Thr Xaa Lys
1 5 10

<210> SEQ ID NO 63
<211> LENGTH: 10
<212> TYPE: PRT
<213> ORGANISM: Artificial Sequence
<220> FEATURE:
<223> OTHER INFORMATION: Peptide compound

<400> SEQUENCE: 63

Ala Lys Pro Ser Tyr Pro Thr Tyr Pro Lys
1 5 10

<210> SEQ ID NO 64
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 64

Ala Lys Pro Ser Tyr Pro Thr Xaa Pro Lys
1 5 10

<210> SEQ ID NO 65
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine

<400> SEQUENCE: 65

Ala Lys Pro Ser Xaa Pro Thr Tyr Pro Lys
1 5 10

<210> SEQ ID NO 66
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE

```
<222> LOCATION: 5,8
<223> OTHER INFORMATION: Wherein Xaa is 3,4-dihydroxyphenylalanine

<400> SEQUENCE: 66

Ala Lys Pro Ser Xaa Pro Thr Xaa Pro Lys
1               5                   10


<210> SEQ ID NO 67
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 7
<223> OTHER INFORMATION: Wherein Xaa is 3-hydroxyproline,
      4-hydroxyproline, or 5-hydroxyproline

<400> SEQUENCE: 67

Ala Lys Pro Ser Tyr Pro Xaa Thr Tyr Lys
1               5                   10


<210> SEQ ID NO 68
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 7
<223> OTHER INFORMATION: Wherein Xaa is 3-hydroxyproline,
      4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 68

Ala Lys Pro Ser Tyr Pro Xaa Thr Xaa Lys
1               5                   10


<210> SEQ ID NO 69
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine
<220> FEATURE:
<221> NAME/KEY: SITE
<222> LOCATION: 7
<223> OTHER INFORMATION: Wherein Xaa is 3-hydroxyproline,
      4-hydroxyproline, or 5-hydroxyproline

<400> SEQUENCE: 69

Ala Lys Pro Ser Xaa Pro Xaa Thr Tyr Lys
1               5                   10


<210> SEQ ID NO 70
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
```

<222> LOCATION: 5,9
<223> OTHER INFORMATION: Wherein Xaa is 3,4-dihydroxyphenylalanine
<220> FEATURE:
<221> NAME/KEY: SITE
<222> LOCATION: 7
<223> OTHER INFORMATION: Wherein Xaa is 3-hydroxyproline,
4-hydroxyproline, or 5-hydroxyproline

<400> SEQUENCE: 70

Ala Lys Pro Ser Xaa Pro Xaa Thr Xaa Lys
1 5 10

<210> SEQ ID NO 71
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6
<223> OTHER INFORMATION: Wherein Xaa is 3-hydroxyproline,
4-hydroxyproline, or 5-hydroxyproline

<400> SEQUENCE: 71

Ala Lys Pro Ser Tyr Xaa Pro Thr Tyr Lys
1 5 10

<210> SEQ ID NO 72
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 6
<223> OTHER INFORMATION: Wherein Xaa is 3-hydroxyproline,
4-hydroxyproline, or 5-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 72

Ala Lys Pro Ser Tyr Xaa Pro Thr Xaa Lys
1 5 10

<210> SEQ ID NO 73
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: SITE
<222> LOCATION: 5
<223> OTHER INFORMATION: Wherein Xaa is 3,4-dihydroxyphenylalanine
<220> FEATURE:
<221> NAME/KEY: SITE
<222> LOCATION: 6
<223> OTHER INFORMATION: Wherein Xaa is 3-hydroxyproline,
4-hydroxyproline, or 5-hydroxyproline

<400> SEQUENCE: 73

Ala Lys Pro Ser Xaa Xaa Pro Thr Tyr Lys
1 5 10

<210> SEQ ID NO 74
<211> LENGTH: 10
<212> TYPE: PRT

-continued

<213> ORGANISM: Artificial Sequence
<220> FEATURE:
<223> OTHER INFORMATION: Peptide compound
<220> FEATURE:
<221> NAME/KEY: SITE
<222> LOCATION: 5,9
<223> OTHER INFORMATION: Wherein Xaa is 3,4-dihydroxyphenylalanine
<220> FEATURE:
<221> NAME/KEY: SITE
<222> LOCATION: 6
<223> OTHER INFORMATION: Wherein Xaa is 3-hydroxyproline,
4-hydroxyproline, or 5-hydroxyproline

<400> SEQUENCE: 74

Ala Lys Pro Ser Xaa Xaa Pro Thr Xaa Lys
1 5 10

<210> SEQ ID NO 75
<211> LENGTH: 4
<212> TYPE: PRT
<213> ORGANISM: Artificial Sequence
<220> FEATURE:
<223> OTHER INFORMATION: Sequence defined by Y
<220> FEATURE:
<221> NAME/KEY: VARIANT
<222> LOCATION: 2,3
<223> OTHER INFORMATION: Wherein Xaa is selected from the group proline,
alanine, 3-hydroxyproline, 4-hydroxyproline, 5-hydroxyproline,
threonine, 3,4-dihydroxyphenylalanine and tyrosine

<400> SEQUENCE: 75

Pro Xaa Xaa Lys
1

<210> SEQ ID NO 76
<211> LENGTH: 4
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is 3-hydroxyproline,
4-hydroxyproline, or 5-hydroxyproline
<220> FEATURE:
<223> OTHER INFORMATION: Sequence defined by Y
<220> FEATURE:
<221> NAME/KEY: VARIANT
<222> LOCATION: 2,3
<223> OTHER INFORMATION: Wherein Xaa is selected from the group proline,
alanine, 3-hydroxyproline, 4-hydroxyproline, 5-hydroxyproline,
threonine, 3,4-dihydroxyphenylalanine and tyrosine

<400> SEQUENCE: 76

Xaa Xaa Xaa Lys
1

<210> SEQ ID NO 77
<211> LENGTH: 4
<212> TYPE: PRT
<213> ORGANISM: Artificial Sequence
<220> FEATURE:
<223> OTHER INFORMATION: Sequence defined by Y
<220> FEATURE:
<221> NAME/KEY: VARIANT
<222> LOCATION: 2,3
<223> OTHER INFORMATION: Wherein Xaa is selected from the group proline,
alanine, 3-hydroxyproline, 4-hydroxyproline, 5-hydroxyproline,
threonine, 3,4-dihydroxyphenylalanine and tyrosine

<400> SEQUENCE: 77

Thr Xaa Xaa Lys
1

<210> SEQ ID NO 78
<211> LENGTH: 4
<212> TYPE: PRT
<213> ORGANISM: Artificial Sequence
<220> FEATURE:
<223> OTHER INFORMATION: Sequence defined by Y
<220> FEATURE:
<221> NAME/KEY: SITE
<222> LOCATION: 3
<223> OTHER INFORMATION: Wherein Xaa is 3,4-dihydroxyphenylalanine

<400> SEQUENCE: 78

Pro Thr Xaa Lys
1

<210> SEQ ID NO 79
<211> LENGTH: 4
<212> TYPE: PRT
<213> ORGANISM: Artificial Sequence
<220> FEATURE:
<223> OTHER INFORMATION: Sequence defined by Y

<400> SEQUENCE: 79

Pro Thr Tyr Lys
1

<210> SEQ ID NO 80
<211> LENGTH: 4
<212> TYPE: PRT
<213> ORGANISM: Artificial Sequence
<220> FEATURE:
<223> OTHER INFORMATION: Sequence defined by Y

<400> SEQUENCE: 80

Thr Tyr Pro Lys
1

<210> SEQ ID NO 81
<211> LENGTH: 4
<212> TYPE: PRT
<213> ORGANISM: Artificial Sequence
<220> FEATURE:
<223> OTHER INFORMATION: Sequence defined by Y
<220> FEATURE:
<221> NAME/KEY: SITE
<222> LOCATION: 2
<223> OTHER INFORMATION: Wherein Xaa is 3,4-dihydroxyphenylalanine

<400> SEQUENCE: 81

Thr Xaa Pro Lys
1

<210> SEQ ID NO 82
<211> LENGTH: 4
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is 3-hydroxyproline,
4-hydroxyproline, or 5-hydroxyproline
<220> FEATURE:
<223> OTHER INFORMATION: Sequence defined by Y

<400> SEQUENCE: 82

Xaa Thr Tyr Lys
1

<210> SEQ ID NO 83
<211> LENGTH: 4
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is 3-hydroxyproline,
4-hydroxyproline, or 5-hydroxyproline
<220> FEATURE:
<223> OTHER INFORMATION: Sequence defined by Y
<220> FEATURE:
<221> NAME/KEY: SITE
<222> LOCATION: 3
<223> OTHER INFORMATION: Wherein Xaa is 3,4-dihydroxyphenylalanine

<400> SEQUENCE: 83

Xaa Thr Xaa Lys
1

<210> SEQ ID NO 84
<211> LENGTH: 4
<212> TYPE: PRT
<213> ORGANISM: Artificial Sequence
<220> FEATURE:
<221> NAME/KEY: SITE
<222> LOCATION: 1
<223> OTHER INFORMATION: Wherein Xaa is 3-hydroxyproline,
4-hydroxyproline, or 5-hydroxyproline
<220> FEATURE:
<223> OTHER INFORMATION: Sequence defined by Y

<400> SEQUENCE: 84

Xaa Thr Ala Lys
1

<210> SEQ ID NO 85
<211> LENGTH: 4
<212> TYPE: PRT
<213> ORGANISM: Artificial Sequence
<220> FEATURE:
<223> OTHER INFORMATION: Sequence defined by Y
<220> FEATURE:
<221> NAME/KEY: SITE
<222> LOCATION: 3
<223> OTHER INFORMATION: Wherein Xaa is 3-hydroxyproline,
4-hydroxyproline, or 5-hydroxyproline

<400> SEQUENCE: 85

Thr Tyr Xaa Lys
1

<210> SEQ ID NO 86
<211> LENGTH: 4
<212> TYPE: PRT
<213> ORGANISM: Artificial Sequence
<220> FEATURE:
<223> OTHER INFORMATION: Sequence defined by Y
<220> FEATURE:
<221> NAME/KEY: SITE
<222> LOCATION: 2
<223> OTHER INFORMATION: Wherein Xaa is 3,4-dihydroxyphenylalanine
<220> FEATURE:
<221> NAME/KEY: SITE
<222> LOCATION: 3
<223> OTHER INFORMATION: Wherein Xaa is 3-hydroxyproline,
4-hydroxyproline, or 5-hydroxyproline

<400> SEQUENCE: 86

Thr Xaa Xaa Lys
1

-continued

```
<210> SEQ ID NO 87
<211> LENGTH: 4
<212> TYPE: PRT
<213> ORGANISM: Artificial Sequence
<220> FEATURE:
<223> OTHER INFORMATION: Sequence defined by Y
<220> FEATURE:
<221> NAME/KEY: SITE
<222> LOCATION: 3
<223> OTHER INFORMATION: Wherein Xaa is 3-hydroxyproline,
      4-hydroxyproline, or 5-hydroxyproline

<400> SEQUENCE: 87

Thr Ala Xaa Lys
1


<210> SEQ ID NO 88
<211> LENGTH: 5
<212> TYPE: PRT
<213> ORGANISM: Artificial Sequence
<220> FEATURE:
<221> NAME/KEY: SITE
<222> LOCATION: 1,4
<223> OTHER INFORMATION: Wherein Xaa is 3-hydroxyproline,
      4-hydroxyproline, or 5-hydroxyproline
<220> FEATURE:
<223> OTHER INFORMATION: Sequence defined by Y

<400> SEQUENCE: 88

Xaa Thr Tyr Xaa Lys
1               5


<210> SEQ ID NO 89
<211> LENGTH: 5
<212> TYPE: PRT
<213> ORGANISM: Artificial Sequence
<220> FEATURE:
<223> OTHER INFORMATION: Sequence defined by Y
<220> FEATURE:
<221> NAME/KEY: SITE
<222> LOCATION: 3
<223> OTHER INFORMATION: Wherein Xaa is 3-hydroxyproline or
      4-hydroxyproline
<220> FEATURE:
<221> NAME/KEY: SITE
<222> LOCATION: 5
<223> OTHER INFORMATION: Wherein Xaa is 3,4-dihydroxyphenylalanine

<400> SEQUENCE: 89

Thr Tyr Xaa Lys Xaa
1               5
```